United States Patent
Chikenji et al.

(10) Patent No.: US 12,090,251 B2
(45) Date of Patent: Sep. 17, 2024

(54) CELL SHEET FOR TRANSPLANTATION INTO LIVING BODY AND METHOD FOR PRODUCING SAME

(71) Applicant: Sapporo Medical University, Sapporo (JP)

(72) Inventors: Takako Chikenji, Sapporo (JP); Mineko Fujimiya, Sapporo (JP); Yuki Saito, Sapporo (JP); Masako Nakano, Sapporo (JP); Naoto Konari, Sapporo (JP); Miho Otani, Sapporo (JP)

(73) Assignee: Sapporo Medical University, Hokkaido (JP)

( * ) Notice: Subject to any disclaimer, the term of this patent is extended or adjusted under 35 U.S.C. 154(b) by 961 days.

(21) Appl. No.: 17/049,867

(22) PCT Filed: Apr. 25, 2019

(86) PCT No.: PCT/JP2019/017594
§ 371 (c)(1),
(2) Date: Oct. 22, 2020

(87) PCT Pub. No.: WO2019/208688
PCT Pub. Date: Oct. 31, 2019

(65) Prior Publication Data
US 2021/0369918 A1    Dec. 2, 2021

(30) Foreign Application Priority Data
Apr. 25, 2018  (JP) .................. 2018-084565

(51) Int. Cl.
| | | |
|---|---|---|
| A61L 27/38 | (2006.01) | |
| A61K 35/28 | (2015.01) | |
| A61L 27/56 | (2006.01) | |
| A61P 13/12 | (2006.01) | |
| A61P 25/28 | (2006.01) | |
| C12M 3/00 | (2006.01) | |
| C12N 5/0775 | (2010.01) | |

(52) U.S. Cl.
CPC .......... *A61L 27/3834* (2013.01); *A61K 35/28* (2013.01); *A61L 27/3878* (2013.01); *A61L 27/56* (2013.01); *A61P 13/12* (2018.01); *A61P 25/28* (2018.01); *C12M 21/08* (2013.01); *C12N 5/0663* (2013.01); *C12N 5/0667* (2013.01); *A61L 2300/64* (2013.01); *A61L 2430/26* (2013.01); *A61L 2430/32* (2013.01)

(58) Field of Classification Search
None
See application file for complete search history.

(56) References Cited

U.S. PATENT DOCUMENTS

| | | |
|---|---|---|
| 2005/0059152 A1 | 3/2005 | Tanavde et al. |
| 2005/0265980 A1 | 12/2005 | Chen et al. |
| 2007/0178591 A1 | 8/2007 | Honmou et al. |
| 2008/0226692 A1* | 9/2008 | Sato .................... C12N 5/0655 435/395 |
| 2010/0254953 A1 | 10/2010 | Honmou et al. |
| 2011/0033523 A1 | 2/2011 | Cantaluppi et al. |
| 2011/0076770 A1 | 3/2011 | Sakai et al. |
| 2011/0129447 A1 | 6/2011 | Meretzki et al. |
| 2013/0072466 A1 | 3/2013 | Choi et al. |
| 2014/0134264 A1 | 5/2014 | Cantaluppi et al. |
| 2014/0295554 A1 | 10/2014 | Kim et al. |
| 2014/0322811 A1 | 10/2014 | Kang et al. |
| 2016/0022738 A1 | 1/2016 | Meretski et al. |
| 2017/0071984 A1 | 3/2017 | Fujimiya et al. |
| 2017/0216362 A1 | 8/2017 | Oka et al. |
| 2017/0319747 A1 | 11/2017 | Kamei et al. |
| 2018/0126039 A1 | 5/2018 | Dufrane |
| 2020/0131470 A1 | 4/2020 | Chikenji et al. |

FOREIGN PATENT DOCUMENTS

| | | |
|---|---|---|
| CN | 103998048 A | 8/2014 |
| CN | 104225681 A1 | 12/2014 |
| CN | 105296415 A | 2/2016 |
| EP | 1857126 A1 | 11/2007 |
| EP | 2308964 A1 | 4/2011 |
| EP | 3090764 A1 | 11/2016 |
| EP | 3117828 A1 | 1/2017 |

(Continued)

OTHER PUBLICATIONS

Jiang, Z., et al., Light-Controlled BMSC Sheet-Implant Complexes with Improved Osteogenesis via an LRP5/ß-Catenin/Runx2 Regulatory Loop, ACS Appl. Mater. Interfaces 2017, 9, 34674-34686; see Jan. 21, 2021 IDS (Year: 2017).*
Jiang et al., "Light-Controlled BMSC Sheet-Implant Complexes with Improved Osteogenesis Via an LRP5/ß-Catenin/Runx2 Regulatory Loop", Application Materials & Interfaces, 9:34674-86 (2017).
Chikenji et al., "Application of Mesenchymal Stem Cells for Diabetic Nephropathy and the Possibility of Developing New Therapeutic Agents", Department of Anatomy, Sapporo Medical University, 12 pages (2019).
Carrion et al., "Autologous Mesenchymal Stem Cell Treatment Increased T Regulatory Cells with No. Effect on Disease Activity in Two Systemic Lupus Erythematosus Patients", Lupus, 2010, vol. 19, pp. 317-322.
Childs et al., "Cellular Senescence in Aging and Age-Related Disease: From Mechanisms to Therapy", Nat. Med., Dec. 2015:21(12), pp. 1424-1435.

(Continued)

*Primary Examiner* — H. Sarah Park
(74) *Attorney, Agent, or Firm* — Buchanan Ingersoll & Rooney PC

(57) ABSTRACT

A cell sheet for transplantation into a living body, containing MSCs having an average cell density of $3.0 \times 10^4$ cells/cm$^2$ or less on the surface of the sheet is provided. A method for producing a cell sheet for transplantation into a living body, including: a step of seeding MSCs on a cell culture carrier having a three-dimensional structure formed of fibers at a cell number of $3.0 \times 10^5$ cells/cm$^2$ or less; and a step of culturing the MSCs and thereby preparing a cell sheet containing the MSCs having an average cell density of $3.0 \times 10^4$ cells/cm$^2$ or less is also provided.

13 Claims, 11 Drawing Sheets

Specification includes a Sequence Listing.

(56) References Cited

FOREIGN PATENT DOCUMENTS

| | | |
|---|---|---|
| JP | 2001072572 A | 3/2001 |
| JP | 2006034111 A | 2/2006 |
| JP | 2006325444 A | 12/2006 |
| JP | 2007325543 A | 12/2007 |
| JP | 2008079598 A | 4/2008 |
| JP | 2009284819 A | 12/2009 |
| JP | 2011502142 A | 1/2011 |
| JP | 2011067175 A | 4/2011 |
| JP | 2011160799 A | 8/2011 |
| JP | 2013018756 A | 1/2013 |
| JP | 2013147479 A | 8/2013 |
| JP | 2013155122 A | 8/2013 |
| JP | 2014018121 A * | 2/2014 |
| JP | 2015089433 A | 5/2015 |
| JP | 2016096732 A | 5/2016 |
| JP | 2017132744 A | 8/2017 |
| JP | 2017221438 A | 12/2017 |
| WO | 2005007176 A1 | 1/2005 |
| WO | 2006093151 A1 | 9/2006 |
| WO | 2006110110 A1 | 10/2006 |
| WO | 2009034708 A1 | 3/2009 |
| WO | 2009057165 A1 | 5/2009 |
| WO | 2009131752 A2 | 10/2009 |
| WO | 2011087103 A1 | 7/2011 |
| WO | 2013009100 A2 | 1/2013 |
| WO | 2014196549 A1 | 12/2014 |
| WO | 2015137419 A1 | 9/2015 |
| WO | 2016068266 A1 | 5/2016 |
| WO | 2016180789 A1 | 11/2016 |
| WO | 2018199194 A1 | 11/2018 |

OTHER PUBLICATIONS

Deng et al., "Bone Marrow Mesenchymal Stromal Cells with CD47 High Expression Via the Signal Transducer and Activators of Transcription Signaling Pathway Preventing Myocardial Fibrosis" Int. J. Clin. Pathol., 2015:8(9), pp. 10555-10564.

Djouad et al., "Reversal of the Immunosuppressive Properties of Mesenchymal Stem Cells by Tumor Necrosis Factor α in Collagen-Induced Arthritis". Arthritis & Rheumatism, vol. 52, No. 5, May 2005, pp. 1595-1603.

Extended European Search Report for European Application No. 15761691.3, dated Oct. 10, 2017, 17 pages.

Ezquer et al., "Systemic Administration of Multipotent Mesenchymal Stromal Cells Reverts Hyperglycemia and Prevents Nephropathy in Type I Diabetic Mice", Biology of Blood and Marrow Transplantation, 14. (2008), pp. 631-640.

Fujimiya et al.. Cardioangiology, 72(4), (2012), pp. 426-430.

Database GenBank, Accession No. NM_000077, dated Aug. 18, 2019, retrieved from the internet Oct. 21, 2019, 7 pages.

Database GenBank, Accession No. NM_058195, dated May 12, 2019, retrieved from the internet Oct. 21, 2019, 6 pages.

Database GenBank, Accession No. NM_001777, dated Aug. 27, 2019, retrieved from the internet Oct. 21, 2019, 8 pages.

Database GenBank, Accession No. NM_001259, dated Sep. 16, 2019, retrieved from the internet Oct. 21, 2019, 7 pages.

Database GenBank, Accession No. NM_000321, dated Sep. 16, 2019. retrieved from the internet Oct. 21, 2019, 11 pages.

Database GenBank, Accession No. NM_000075, dated Oct. 14, 2019, retrieved from the internet Oct. 21. 2019, 4 pages.

Hao et al., "Culturing on Wharton's Jelly Extract Delays Mesenchymal Stem Cell Senescence Through p53 and p16 INK4a/pRb Pathways", PLOS One, Mar. 2013, vol. 8, Issue 3, 11 pages.

Hara et al., "Regulation of p16$^{cDKN}$ Expression and Its Implications For Cell Immortalization and Senescence" Molecular and Cellular Biology, Mar. 1996, pp. 859-867.

International Search Report and Written Opinion for International Application No. PCT/JP2015/057217, dated Jun. 16, 2015, 9 pages.

International Search Report and Written Opinion for International Application No. PCT/JP2018/016883, dated Jul. 24. 2018, 8 pages.

Kawakatsu et al., "Placental Extract Protects Bone Marrow-Derived Stem/Progenitor Cells Against Radiation Injury Through Anti-Inflammatory Activity", Journal of Radiation Research, 2013, 54, pp. 268-276.

Kim et al., "Protective Effects of Human Placenta Extract on Cartilage Degradation in Experimental Osteoarthritis", Biol. Pharm. Bull., 33(6), (2010), pp. 1004-1010.

Kim et al., "Alternative Xeno-Free Biomaterials Derived From Human Umbilical Cord for the Self-Renewal Ex-vivo Expansion of Mesenchymal Stem Cells", Stem Cells and Development, vol. 22, No. 22, 2013, pp. 3025-3038.

Kim et al., "Restoration of Angiogenic Capacity of Diabetes-Insulted Mesenchymal Stem Cells by Oxytocin", BMC Cell Biology, 2013, 14:38, 11 pages.

Klinkhammer et al., "Mesenchymal Stem Cells from Rats with Chronic Kidney Disease Exhibit Premature Senescence and Loss of Regenerative Potential", PLOS One, Mar. 2014, vol. 9(3): e92115, 12 pages.

Lee et al., "Mutipotent Stromal Cells From Human Marrow Home to and Promote Repair of Pancreatic Islets and Renall Glomeruli in Diabetic NOD/scid Mice", PNAS, Nov. 14, 2006, vol. 103, No. 46, pp. 17438-17443.

Nagaishi et al., Regenerative Medicine, vol. 13, Special Extra Issue, (2014), 3 pages.

Noh et al., "Uremia Induces Functional Incompetence of Bone Marrow-Derived Stromal Cells", Nephrol Dial Transplant, (2012), 27, pp. 218-225.

Oritz et al., "Mesenchymal Stem Cell Engraftment in Lung is Enhanced in Response to Bleomycin Exposure and Ameliorates Its Fibrotic Effects", PNAS, Jul. 8, 2003, vol. 100, No. 14, pp. 8407-8411.

Phadnis et al., "Mesenchymal Stem Cells Derived From Bone Marrow of Diabetic Patients Portrait Unique Markers Influenced by the Diabetic Microenvironment", The Review of Diabetic Studies, vol. 6, No. 4, (2009), 11 pages.

Ra et al., "Stem Cell Treatment of Patients with Autoimmune Disease by Systemic Infusion of Culture-Expanded Autologous Adipose Tissue Derived Mesenchymal Stem Cells", Journal of Translational Medicine (2011), 9:181, 11 pages.

Shin et al., "Culture and in vitro Hepatogenic Differentiation of Placenta-Derived Stem Cells, Using Placental Extract As An Alternative to Serum", Cell Prolif., (2010). 43, pp. 435-444.

Stenderup et al., "Aging is Associated with Decreased Maximal Life Span and Accelerated Senescence of Bone Marrow Stromal Cells", Bone 33, (2003), pp. 919-926.

Sun et al., Database Medicine XP-002773912, (2007), 1 page.

Tanaka et al., "Myogenic Lineage Differentiated Mesenchymal Stem Cells Enhance Recovery from Dextran Sulfate Sodium-Induced Colitis In The Rat", J. Gastroenterol, (2011), 46, pp. 143-152.

Watanabe et al., "Conditioned Mesenchymal Stem Cells Produce Pleiotropic Gut Tropic Factors", J. Gastroenternal, (2014), 49, pp. 270-282.

Zappia et al., "Mesenchymal Stem Cells Ameliorate Experimental Autoimmune Encephalomyelitis Inducing T-Cell Anergy", Blood, Sep. 1, 2005, vol. 106, No. 5, pp. 1755-1761.

International Preliminary Report on Patentability and Written Opinion for International Application No. PCT/JP2018/016883, issued Oct. 29, 2019, 10 pages.

Liu L., et al., "Nano-On-Micro Fibrous Extracellular Matrices for Scalable Expansion of Human ES/IPS Cells", Biomaterials (2017), 124, pp. 47-54.

Tidbal et al., Shifts in Macrophage Cytokine Production Drive Muscle Fibrosis, Nature Medicine, 21(7):665-666 (2015).

Meng et al., "Inflammatory Processes in Renal Fibrosis", Nature Reviews, Nephrology, (2014).

Pellicoro et al., "Liver Fibrosis and Repair: Immune Regulation of Wound Healing in a Solid Organ", Nature Reviews, Immunnology, 14:181-194 (2014).

Sobolewski et al., "Wharton's Jelly as a Reservoir of Peptide Growth Factors". Placenta (2005), 26, 747-752.

Chinese Office Action for Chinese Application No. 201880026731. X, dated Sep. 7, 2022 with translation, 23 pages.

(56) References Cited

OTHER PUBLICATIONS

Chinese Office Action for Chinese Application No. 201980027720. 8, dated Nov. 4, 2022 with translation, 17 pages.

Tokalov, S.V. et al., "Age-Related Changes in the Frequency of Mesenchymal Stem Cells in the Bone Marrow of Rats", Stem Cells and Development, 2007, 16:439-446.

Japanese Notice of Reasons for Refusal for Japanese Application No. 2020-515557, dated Apr. 4, 2023 with translation, 6 pages.

Taiwanese Office Action for Taiwanese Application No. 108114451, dated Apr. 18, 2023 with translation, 13 pages.

Chinese Office Action for Chinese Application No. 201880026731. X, dated Feb. 9, 2023 with translation, 20 pages.

Ksiazek, "A Comprehensive Review on Mesenchymal Stem Cell Growth and Senescence", Rejuvenation Research, 12(2):105-117 (2009).

Sepúlveda et al., "Cell Senescence Abrogates the Therapeutic Potential of Human Mesenchymal Stem Cells In the Lethal Endotoxemia Model", Stem Cells, 32(7):1865-1877 (2014).

Shibata et al., "Expression of the p16INK4A Gene Is Associated Closely With Senescence of Human Mesenchymal Stem Cells and Is Potentially Silenced by DNA Methylation During In Vitro Expansion", Stem Cells, 25:2371-2382 (2007).

Non Final Office Action for U.S. Appl. No. 16/607,244, mailed Dec. 10, 2021, 31 pages.

Hori et al., "Interaction Between Cells and Non-Woven Fabrics Promotes Mesenchymal Stem Growth Factor Production" with translation, The 17th Annual Meeting of the Japanese Society for Regenerative Medicine, 2 pages (2018).

Imahuku et al., "Therapeutic Efficacy of Allogeneic Bone Marrow-Derived Mesenchymal Stem Cell Sheet Transplantation in a Rat Model of Renal Ischemia-Reperfusion Injury" with translation, The 17th Annual Meeting of the Japanese Society for Regenerative Medicine, 2 pages (2018).

Ito et al., "Application of Cell Sheet Technology to Bone Marrow Stromal Cell Transplantation for Rat Brain Effect", Journal of Tissue Engineering and Regenerative Medicine, 11:375-381 (2017).

Japanese Notice of Reasons for Refusal for Japanese Application No. 2019-514592, dated May 17, 2022 with translation, 8 pages.

Nagaishi et al., "Mesenchymal Stem Cell Therapy Ameliorates Diabetic Nephropathy Via the Paracrine Effect of Renal Tropic Factors Including Exosomes", Scientific Reports, 6(1): 16 pages (2016).

Extended European Search Report for European Application No. 18789904.2, dated Dec. 21, 2020, 7 pages.

Extended European Search Report for European Application No. 19793215.5, dated Jan. 19, 2022, 10 pages.

Korean Office Action for Korean Application No. 10-2020-7033876, issued Jan. 15, 2024 with English translation, 21 pages.

* cited by examiner proximal tubular epithelium with distinct microvilli decrease in inflammatory cells in tubular interstitium

SEQUENCE LISTING

```
<160> NUMBER OF SEQ ID NOS: 26

<210> SEQ ID NO 1
<211> LENGTH: 18
<212> TYPE: DNA
<213> ORGANISM: Artificial Sequence
<220> FEATURE:
<223> OTHER INFORMATION: OCT4 Forward Primer

<400> SEQUENCE: 1
gacaggggag gggaggag                                                        18

<210> SEQ ID NO 2
<211> LENGTH: 21
<212> TYPE: DNA
<213> ORGANISM: Artificial Sequence
<220> FEATURE:
<223> OTHER INFORMATION: OCT4 Reverse Primer

<400> SEQUENCE: 2
cttccctcca accagttgcc c                                                    21

<210> SEQ ID NO 3
<211> LENGTH: 21
<212> TYPE: DNA
<213> ORGANISM: Artificial Sequence
<220> FEATURE:
<223> OTHER INFORMATION: NANOG Forward Primer

<400> SEQUENCE: 3
tggacactgg ctgaatcctt c                                                    21

<210> SEQ ID NO 4
<211> LENGTH: 21
<212> TYPE: DNA
<213> ORGANISM: Artificial Sequence
<220> FEATURE:
<223> OTHER INFORMATION: NANOG Reverse Primer

<400> SEQUENCE: 4
cgttgattag gctccaacca t                                                    21

<210> SEQ ID NO 5
```

```
<211> LENGTH: 20
<212> TYPE: DNA
<213> ORGANISM: Artificial Sequence
<220> FEATURE:
<223> OTHER INFORMATION: SOX2 Forward Primer

<400> SEQUENCE: 5
gggaaatggg aggggtgcaa                                              20

<210> SEQ ID NO 6
<211> LENGTH: 20
<212> TYPE: DNA
<213> ORGANISM: Artificial Sequence
<220> FEATURE:
<223> OTHER INFORMATION: SOX2 Reverse Primer

<400> SEQUENCE: 6
ttgcgtgagt gtggatggga                                              20

<210> SEQ ID NO 7
<211> LENGTH: 22
<212> TYPE: DNA
<213> ORGANISM: Artificial Sequence
<220> FEATURE:
<223> OTHER INFORMATION: DNMT1 Forward Primer

<400> SEQUENCE: 7
cgtaaagaag aattatccga gg                                           22

<210> SEQ ID NO 8
<211> LENGTH: 21
<212> TYPE: DNA
<213> ORGANISM: Artificial Sequence
<220> FEATURE:
<223> OTHER INFORMATION: DNMT1 Reverse Primer

<400> SEQUENCE: 8
gttttctaga cgtccattca c                                            21

<210> SEQ ID NO 9
<211> LENGTH: 18
<212> TYPE: DNA
<213> ORGANISM: Artificial Sequence
<220> FEATURE:
<223> OTHER INFORMATION: TERT1 Forward Primer

<400> SEQUENCE: 9
cggaagagtg tctggagc                                                18

<210> SEQ ID NO 10
<211> LENGTH: 19
<212> TYPE: DNA
<213> ORGANISM: Artificial Sequence
<220> FEATURE:
<223> OTHER INFORMATION: TERT1 Reverse Primer

<400> SEQUENCE: 10
ggatgaagcg gagtctgga                                               19

<210> SEQ ID NO 11
<211> LENGTH: 24
<212> TYPE: DNA
<213> ORGANISM: Artificial Sequence
<220> FEATURE:
<223> OTHER INFORMATION: IL-6 Forward Primer

<400> SEQUENCE: 11
```

```
gatgagtaca aaagtcctga tcca                                          24

<210> SEQ ID NO 12
<211> LENGTH: 19
<212> TYPE: DNA
<213> ORGANISM: Artificial Sequence
<220> FEATURE:
<223> OTHER INFORMATION: IL-6 Reverse Primer

<400> SEQUENCE: 12
ctgcagccac tggttctgt                                                19

<210> SEQ ID NO 13
<211> LENGTH: 24
<212> TYPE: DNA
<213> ORGANISM: Artificial Sequence
<220> FEATURE:
<223> OTHER INFORMATION: IDO Forward Primer

<400> SEQUENCE: 13 gcattttca gtgttcttcg cata                                           24

<210> SEQ ID NO 14
<211> LENGTH: 24
<212> TYPE: DNA
<213> ORGANISM: Artificial Sequence
<220> FEATURE:
<223> OTHER INFORMATION: IDO Reverse Primer

<400> SEQUENCE: 14
tcatacacca gaccgtctga tagc                                          24

<210> SEQ ID NO 15
<211> LENGTH: 26
<212> TYPE: DNA
<213> ORGANISM: Artificial Sequence
<220> FEATURE:
<223> OTHER INFORMATION: TSG-6 Forward Primer

<400> SEQUENCE: 15
cccattgtga agccagggcc caactg                                        26

<210> SEQ ID NO 16
<211> LENGTH: 27
<212> TYPE: DNA
<213> ORGANISM: Artificial Sequence
<220> FEATURE:
<223> OTHER INFORMATION: TSG-6 Reverse Primer

<400> SEQUENCE: 16
ggaagctcat ctccacagta tcttccc                                       27

<210> SEQ ID NO 17
<211> LENGTH: 20
<212> TYPE: DNA
<213> ORGANISM: Artificial Sequence
<220> FEATURE:
<223> OTHER INFORMATION: P16INK4a Forward Primer

<400> SEQUENCE: 17
agcatggagc cttcggctga                                               20

<210> SEQ ID NO 18
<211> LENGTH: 21
<212> TYPE: DNA
```

```
<213> ORGANISM: Artificial Sequence
<220> FEATURE:
<223> OTHER INFORMATION: P16INK4a Reverse Primer

<400> SEQUENCE: 18
ccatcatcat gacctggatc g                                              21

<210> SEQ ID NO 19
<211> LENGTH: 20
<212> TYPE: DNA
<213> ORGANISM: Artificial Sequence
<220> FEATURE:
<223> OTHER INFORMATION: P21 Forward Primer

<400> SEQUENCE: 19
gagactctca gggtcgaaaa                                                20

<210> SEQ ID NO 20
<211> LENGTH: 20
<212> TYPE: DNA
<213> ORGANISM: Artificial Sequence
<220> FEATURE:
<223> OTHER INFORMATION: P21 Reverse Primer

<400> SEQUENCE: 20
ttagggcttc ctcttggaga                                                20

<210> SEQ ID NO 21
<211> LENGTH: 21
<212> TYPE: DNA
<213> ORGANISM: Artificial Sequence
<220> FEATURE:
<223> OTHER INFORMATION: TP53 Forward Primer

<400> SEQUENCE: 21
tgactgtacc accatccact a                                              21

<210> SEQ ID NO 22
<211> LENGTH: 18
<212> TYPE: DNA
<213> ORGANISM: Artificial Sequence
<220> FEATURE:
<223> OTHER INFORMATION: TP53 Reverse Primer

<400> SEQUENCE: 22
aaacacgcac ctcaaagc                                                  18

<210> SEQ ID NO 23
<211> LENGTH: 20
<212> TYPE: DNA
<213> ORGANISM: Artificial Sequence
<220> FEATURE:
<223> OTHER INFORMATION: aSMA Forward Primer

<400> SEQUENCE: 23
gcagcccagc caagcactgt                                                20

<210> SEQ ID NO 24
<211> LENGTH: 20
<212> TYPE: DNA
<213> ORGANISM: Artificial Sequence
<220> FEATURE:
<223> OTHER INFORMATION: aSMA Reverse Primer

<400> SEQUENCE: 24
tgggagcatc gtccccagca                                                20
```

```
<210> SEQ ID NO 25
<211> LENGTH: 20
<212> TYPE: DNA
<213> ORGANISM: Artificial Sequence
<220> FEATURE:
<223> OTHER INFORMATION: RNA18S Forward Primer

<400> SEQUENCE: 25
atcggggatt gcaattattc                                               20

<210> SEQ ID NO 26
<211> LENGTH: 20
<212> TYPE: DNA
<213> ORGANISM: Artificial Sequence
<220> FEATURE:
<223> OTHER INFORMATION: RNA18S Reverse Primer

<400> SEQUENCE: 26
ctcactaaac catccaatcg                                               20
```

CELL SHEET FOR TRANSPLANTATION INTO LIVING BODY AND METHOD FOR PRODUCING SAME

CROSS-REFERENCE TO RELATED APPLICATIONS

This application is a U.S. national phase application of International Application No. PCT/JP2019/017594, filed Apr. 25, 2019 claiming the benefit of Japanese Application No. 2018-084565, filed Apr. 25, 2018, the contents of each of which are incorporated herein by their entireties for all purposes.

The Sequence Listing for this application is labeled "BCL-113US-P17SM01WO_ST25" which was created on Oct. 20, 2020 and is 5.09 KB. The entire contents of the sequence listing are incorporated herein by reference in their entireties.

FIELD

The present invention relates to a cell sheet for transplantation into a living body and a method for producing the same.

BACKGROUND

Mesenchymal stem cells (hereinafter, may also be referred to as MSCs) are stem cells having multipotency and self-replication ability. MSCs can differentiate into not only cells belonging to the mesenchyme such as osteoblasts, chondrocytes, adipocytes, and myocytes, but also neurons, hepatocytes, and the like, beyond germ layers. MSCs are also known to have paracrine effects via humoral factors produced by the MSCs themselves, and cell adhesive interactions. On the basis of these actions, MSCs exhibit the ability to repair and regenerate target tissues and cells, and immune regulatory ability such as anti-inflammation. As a result, MSCs are expected to have a therapeutic effect on various diseases.

MSCs are easily isolated in culture and have high proliferation potency, therefore the number of transplantable cells can be secured in a short period of time. MSCs also allow autologous transplantation without immune rejection, and have fewer ethical issues. Moreover, allogeneic transplantation of MSCs is practical as there is no requirement for a pretreatment due to their low immunogenicity. For such reasons, MSCs are seen as an ideal material for cell transplantation therapies, and the applications of MSCs in treating various diseases are under investigation.

One of the diseases to which cell transplantation therapies using MSCs is potentially applicable is kidney disease, in particular, chronic kidney disease. The chronic kidney disease is a state in which renal impairment represented by proteinuria and/or renal dysfunction measured in glomerular filtration rates continue for three months or more. One in eight adults is suffering from the disease in Japan. When the symptoms of chronic kidney disease progress and reach end-stage renal failure, drug treatment is no longer effective. Many patients have no choice but undergo dialysis, which is a palliative treatment. Thus, patients with chronic renal failure need to undergo dialysis for the rest of their lives, and considerable physical and economic burdens are imposed on them. Furthermore, the increasing cost of dialysis care has become a concern for the medical economy.

In the process of establishing cell transplantation therapies using MSCs, the inventors of the present invention have found that patients (e.g., diabetic patients) have abnormal MSCs, specifically, such patients have MSCs in which the above diverse capabilities are lost, or these capabilities are reduced compared to those of normal MSCs, and thereby their therapeutic effect on diseases is lost, or is reduced compared to those of the normal MSCs. Further, the present inventors have found that an extract from a mammalian fetal appendage can activate the abnormal MSCs and restore their therapeutic effect, and that the activated MSCs can be used for autologous transplantation therapies. Thus, the inventors of the present invention have invented an activator for abnormal MSCs and filed for a patent (refer to Patent Literature 1). This activator contains an extract from a mammalian fetal appendage as an active ingredient. The activator is particularly significant as it enables autologous transplantation of MSCs even for patients in a stage requiring a medical treatment.

In cell transplantation therapies, to reduce the amount of MSCs to be used, locally applicable formulations capable of concentrating the MSCs on a required site are under investigation. As a cell transplantation therapy for kidney disease using MSCs, an approach of treating kidney disease by applying a cell sheet composition containing MSCs on the kidney has been reported (refer to Patent Literature 2). The cell sheet composition is prepared by seeding and culturing MSCs on a stimulus-responsive culture substrate, and detaching the cells by detachment stimulation.

CITATION LIST

Patent Literature

Patent Literature 1: WO 2015/137419
Patent Literature 2: Japanese Patent Application Laid-open No. 2017-132744

SUMMARY

Technical Problem

An object of the present invention is to provide a novel cell sheet for transplantation into a living body, containing MSCs with high therapeutic effect.

Solution to Problem

The inventors of the present invention have found that it is possible to produce MSC cell sheets with high therapeutic effect on diseases, by culturing MSCs on a specific culture carrier at specific low cell density, and have completed the following inventions.

(1) A cell sheet for transplantation into a living body, containing MSCs having an average cell density of $3.0 \times 10^4$ cells/cm$^2$ or less on the surface of the sheet.
(2) The cell sheet according to (1), further contains a biocompatible support.
(3) The cell sheet according to (2), wherein the support is a cell culture carrier having a three-dimensional structure formed of a fiber.
(4) The cell sheet according to (3), wherein the cell culture carrier has openings formed of a fiber having an average fiber diameter of from nanometer order to micrometer order on the cell contact surface.
(5) The cell sheet according to (4), wherein the openings have an average diameter ranging from 500 nm to 1,000 µm.

(6) The cell sheet according to any one of (2) to (5), wherein the support is a cell culture carrier containing a nanofiber made of a biodegradable polymer.

(7) The cell sheet according to any one of (1) to (6), containing MSCs having an average cell density ranging from $1.0 \times 10^3$ cells/cm$^2$ to $3.0 \times 10^4$ cells/cm$^2$ on the surface of the sheet, for use in treating kidney disease.

(8) The cell sheet according to (7), wherein the cell sheet is applied under the kidney fibrous capsule.

(9) The cell sheet according to any one of (1) to (6), containing MSCs having an average cell density ranging from $0.5 \times 10^3$ cells/cm$^2$ to $1.5 \times 10^4$ cells/cm$^2$ on the surface thereof, for use in treating brain injury or neurodegenerative disease.

(10) The cell sheet according to (9), wherein the cell sheet is applied to a site of brain injury, a site of brain degeneration, or the vicinity thereof.

(11) The cell sheet according to any one of (1) to (10), wherein the MSCs are MSCs derived from bone marrow or adipose tissue.

(12) The cell sheet according to any one of (1) to (11), wherein the MSCs are MSCs separated from a subject suffering from a disease.

(13) A method for producing a cell sheet for transplantation into a living body, including: a step of seeding MSCs on a cell culture carrier having a three-dimensional structure formed of fibers at a cell number of $3.0 \times 10^5$ cells/cm$^2$ or less; and a step of culturing the MSCs and thereby preparing a cell sheet containing the MSCs having an average cell density of $3.0 \times 10^4$ cells/cm$^2$ or less.

(14) The method according to (13), wherein the cell culture carrier has openings formed of a fiber having an average fiber diameter of from nanometer order to micrometer order on the cell contact surface.

(15) The method according to (14), wherein the openings have an average diameter ranging from 500 nm to 1,000 μm.

(16) The method according to any one of (13) to (15), wherein the cell culture carrier is a cell culture carrier containing a nanofiber made of a biodegradable polymer.

(17) The method according to any one of (13) to (16), wherein the MSCs are MSCs derived from bone marrow or adipose tissue.

(18) The method according to any one of (13) to (17), wherein the MSCs are MSCs separated from a subject suffering from a disease.

Advantageous Effects of Invention

According to the present invention, a cell sheet with high therapeutic effect can be produced, and the cell number of MSCs required in transplantation therapy can be greatly reduced than that in conventional transplantation therapies. Furthermore, according to the present invention, even chronic kidney disease having reached end-stage kidney failure that has otherwise no curative therapy except for kidney transplantation, leading patients to undergo dialysis for the rest of their lives, can be treated.

DESCRIPTION OF EMBODIMENTS

Figure 1:
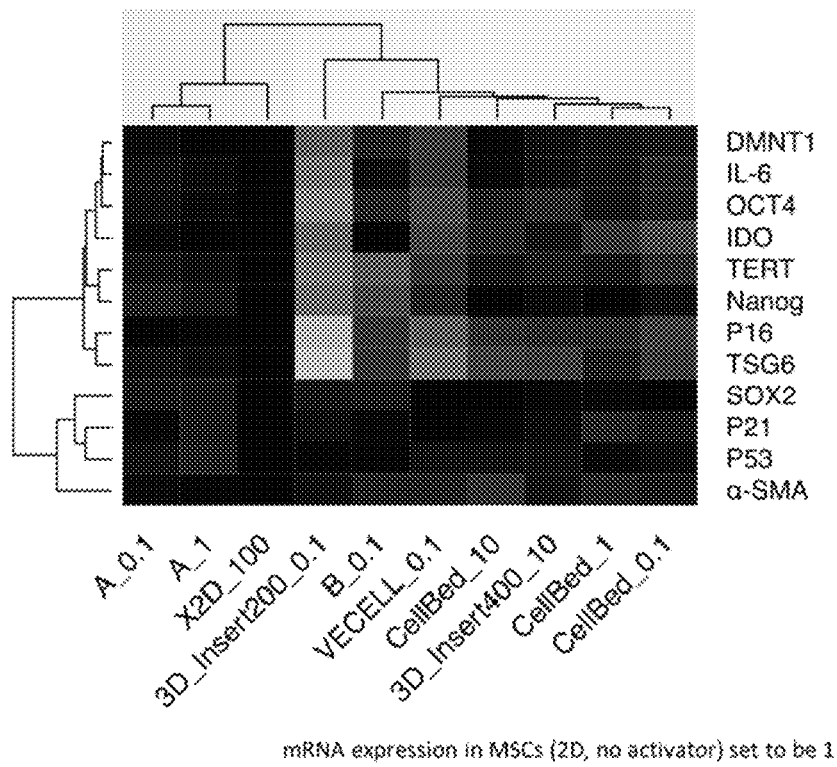
FIG. 1 is a diagram illustrating the result of cluster analysis of gene expression profiles of MSCs from a patient with osteoarthritis of hip (hereinafter, may be referred to as OA-MSCs), cultured on cell culture carriers having a three-dimensional structure formed of fibers (hereinafter, may also be referred to as three-dimensional culture carriers) or on a cell culture carrier of a comparative example, in the presence of an activator.

Cell Sheet for Transplantation into Living Body

A first aspect of the present invention relates to a cell sheet for transplantation into a living body, containing MSCs having an average cell density of $3.0 \times 10^4$ cells/cm$^2$ or less on the surface thereof (hereinafter, simply referred to as a cell sheet).

The cell sheet contains MSCs (MSC population) having an average cell density of $3.0 \times 10^4$ cells/cm$^2$ or less on the surface thereof. The average cell density of MSCs is an arithmetic mean value of the cell number of MSCs per unit area of the cell sheet. The average cell density can be calculated by counting the number of MSCs identified on the cell sheet surface through microscopic observation and the like, and dividing the total number by the area of the entire cell sheet. Alternatively, the average cell density can also be calculated by observing the cell sheet surface through a microscope and the like, and counting the number of MSCs on unit area of the cell sheet surface through microscopic observation and the like.

In the present invention, the average cell density of MSCs on the cell sheet surface may be $3.0 \times 10^4$ cells/cm$^2$ or less. For example, the average cell density of MSCs can be suitably set from $0.1 \times 10^3$ cells/cm$^2$ to $3.0 \times 10^4$ cells/cm$^2$, from $0.1 \times 10^3$ cells/cm$^2$ to $2.0 \times 10^4$ cells/cm$^2$, from $0.1 \times 10^3$ cells/cm$^2$ to $1.5 \times 10^4$ cells/cm$^2$, from $0.1 \times 10^3$ cells/cm$^2$ to $1.0 \times 10^4$ cells/cm$^2$, from $0.1 \times 10^3$ cells/cm$^2$ to $0.5 \times 10^4$ cells/cm$^2$, from $0.3 \times 10^3$ cells/cm$^2$ to $3.0 \times 10^4$ cells/cm$^2$, from $0.5 \times 10^3$ cells/cm$^2$ to $3.0 \times 10^4$ cells/cm$^2$, from $1.0 \times 10^3$ cells/cm$^2$ to $3.0 \times 10^4$ cells/cm$^2$, from $3.0 \times 10^3$ cells/cm$^2$ to $3.0 \times 10^4$ cells/cm$^2$, from $6.0 \times 10^3$ cells/cm$^2$ to $3.0 \times 10^4$ cells/cm$^2$, from $1.0 \times 10^4$ cells/cm$^2$ to $3.0 \times 10^4$ cells/cm$^2$, from $0.3 \times 10^3$ cells/cm$^2$ to $2.0 \times 10^4$ cells/cm$^2$, from $0.5 \times 10^3$ cells/cm$^2$ to $2.0 \times 10^4$ cells/cm$^2$, from $1.0 \times 10^3$ cells/cm$^2$ to $2.0 \times 10^4$ cells/cm$^2$, from $3.0 \times 10^3$ cells/cm$^2$ to $2.0 \times 10^4$ cells/cm$^2$, from $6.0 \times 10^3$ cells/cm$^2$ to $2.0 \times 10^4$ cells/cm$^2$, and the like. The average cell density of MSCs on the cell sheet surface is preferably from $0.5 \times 10^3$ to $3.0 \times 10^4$ cells/cm$^2$, more preferably from $0.5 \times 10^3$ to $2.0 \times 10^4$ cells/cm$^2$, further preferably from $2.0 \times 10^3$ cells/cm$^2$ to $2.0 \times 10^4$ cells/cm$^2$, still preferably from $2.0 \times 10^3$ cells/cm$^2$ to $1.8 \times 10^4$ cells/cm$^2$, still more preferably from $3.0 \times 10^3$ cells/cm$^2$ to $1.6 \times 10^4$ cells/cm$^2$, still further preferably from $3.0 \times 10^3$ cells/cm$^2$ to $1.0 \times 10^4$ cells/cm$^2$, and particularly preferably from $3.0 \times 10^3$ cells/cm$^2$ to $8.0 \times 10^3$ cells/cm$^2$.

The average cell density may also be expressed by the MSC coverage (confluency) on the cell sheet surface. Confluence or 100% confluency is a state when the cell sheet surface is completely covered with MSCs, and the MSCs are in close contact with each other. The relative cell density with respect to the confluence or 100% confluency is percentage confluency, and can be calculated by dividing the sum of the area covered with the MSCs on the cell sheet surface by the area of the entire sheet.

In a case of MSCs derived from human bone marrow, the average cell density $2.0 \times 10^4$ cells/cm$^2$ corresponds to 60% confluency. Similarly, the average cell density ranging from $1.0 \times 10^3$ to $2.0 \times 10^4$ cells/cm$^2$ corresponds to 10 to 60% confluency, the average cell density ranging from $1.0 \times 10^3$ cells/cm$^2$ to $1.6 \times 10^4$ cells/cm$^2$ corresponds to 10 to 50% confluency, the average cell density ranging from $1.0 \times 10^3$ cells/cm$^2$ to $1.0 \times 10^4$ cells/cm$^2$ corresponds to 10 to 40% confluency, the average cell density ranging from $3.0 \times 10^3$ cells/cm$^2$ to $1.0 \times 10^4$ cells/cm$^2$ corresponds to 20 to 40% confluency, and the average cell density ranging from $3.0 \times 10^3$ cells/cm$^2$ to $8.0 \times 10^3$ cells/cm$^2$ corresponds to 20 to 35% confluency.

Thus, the cell sheet according to the present invention containing MSCs having an average cell density of $2.0 \times 10^4$ cells/cm$^2$ or less on the surface thereof, may also be referred to as a cell sheet containing MSCs the cell density of which is 60% confluency or less on the surface thereof. In a preferred embodiment, the cell sheet according to the present invention contains MSCs the cell density on which is 10 to 60% confluency, 10 to 50% confluency, 10 to 40% confluency, 20 to 40% confluency, and 20 to 35% confluency on the surface thereof.

The cell sheet may also contain cells other than the MSCs, as long as the cell sheet contains MSCs having an average cell density of $3.0 \times 10^4$ cells/cm$^2$ or less on the surface thereof. The cells other than the MSCs may be cells derived from tissue from which the MSC are isolated, or may be cells added in the hope of obtaining desirable effects when used in combination with MSCs. For example, the latter cells include vascular endothelial cells, fibroblasts, and epithelial cells, and are suitably selected according to the disease to be treated or the site where transplantation takes place.

An example of the cell sheet according to the present invention is a sheet consisting of MSCs adhering to each other via the extracellular matrix produced by the MSCs themselves, or via the extracellular matrix added to an culture medium in culture.

Another example of the cell sheet according to the present invention is a cell sheet further containing a biocompatible support. In this example, the cell sheet may also be a combination of MSCs adhering to each other via the extracellular matrix and a support.

Alternatively, the cell sheet may be obtained by integrating a support and MSCs, such as by adhering MSCs to the surface of a sheet-shaped support, and by embedding a part or the whole of an MSC cell body in a hollow or an opening formed on the support surface. A cell sheet such as the above one in a state in which a part or the whole of an MSC cell body is embedded in a hollow or an opening formed on the support surface is also encompassed by the cell sheet "containing MSCs on the surface thereof" according to the present invention, as an aspect. Thus, the cell sheet according to the present invention is a cell sheet in a state in which MSCs adhere to each other via the extracellular matrix or in a state in which MSCs are integrally formed with a support.

The cell sheet according to the present invention is distinguishable from a culture carrier merely having MSCs seeded for cell culture.

The support contained in the cell sheet according to the present invention is not limited as long as the support is made of a biocompatible material and is formed in a sheet-like shape. The shape, size, and thickness of the support are not limited as long as the support can be easily handled in the subsequent transplantation into a living body. Examples of the biocompatible material include a polymer compound such as polyfluoroethylene and polystyrene, an inorganic compound such as silica, and a biodegradable polymer. Among these, the biodegradable polymer is preferable. Examples of the biodegradable polymer include a synthetic polymer material such as polyglycolic acid, polylactic acid, polyethylene glycol, polycaprolactone, polydioxanone, and a copolymer of the materials described above such as a lactic-co-glycolic acid copolymer; an inorganic material such as β-tricalcium phosphate and calcium carbonate; and a natural polymeric material such as collagen, gelatin, alginic acid, hyaluronic acid, agarose, chitosan, fibrin, fibroin, chitin, cellulose, and silk.

A preferred example of the support contained in the cell sheet according to the present invention is a sheet-shaped cell culture carrier having a three-dimensional structure formed of fibers. In particular, it is preferable to use a sheet-shaped three-dimensional culture carrier formed of fibers with an average fiber diameter of from nanometer (nm) order to micrometer (μm) order. The cell culture carrier or culture carrier is a carrier used for cell culture, serving as a scaffold to which cells adhere. The "average fiber diameter" means an arithmetic mean value of fiber diameter measured as the length in a direction orthogonal to the length direction of fibers, when the culture carrier is observed from the cell contact surface side, typically from the upper side. Unless otherwise specified, the average herein means the number average. A preferred example of the support in the present invention also includes a three-dimensional culture carrier that is formed of fibers with an average fiber diameter of from nanometer (nm) order to micrometer (μm) order, and that has openings formed of the fibers and formed on the contact surface with cells. In this example, the "opening" refers to a concavity that is formed of the fibers described above and that is present on the contact surface with the cells in the carrier.

When the fibers are in contact with each other, the average diameter of the openings means an average value of diameters of figures outlined by fibers, identified when the culture carrier is observed from above. As for a polygonal figure, the diameter of the figure corresponds to an arithmetic mean value of the lengths of the diagonals from the vertices. As for a circle figure, the diameter of the figure corresponds to its diameter. As for an oval or similar figure, the diameter of the figure corresponds to its long diameter.

When the fibers are not in contact with each other, the average diameter of the openings means a mean flow pore size obtained by a method defined in ASTM-F316. For example, the mean flow pore size can be measured by a mean flow point method using a porometer (manufacture by Coulter Electronics and the like).

The average fiber diameter of fibers that form the three-dimensional culture carrier may be in the range of nm to μm, preferably 10 nm to 500 μm, and more preferably 10 nm to 300 μm. In certain embodiments, for example, the average fiber diameter may be in the range of 10 nm to 1 μm, 100 nm to 1 μm, 500 nm to 1 μm, 1 μm to 10 μm, 1 μm to 100 μm, 1 μm to 300 μm, or 1 μm to 500 μm. The average fiber diameter may preferably be in the range of 10 nm to 1 μm, 1 μm to 10 μm, or 10 μm to 300 μm. In the present invention, fibers generally called nanofibers can be used.

In the three-dimensional culture carrier having openings on the contact surface with cells, the average diameter of the openings may be in the range of 500 nm to 1,000 μm, preferably 700 nm to 600 μm, and more preferably 900 nm to 400 μm. In certain embodiments, for example, the average diameter of the openings may be in the range of 500 nm to 100 μm, 5 μm to 100 μm, 10 μm to 100 μm, 20 μm to 100 μm, 100 μm to 200 μm, 100 μm to 400 μm, or 100 μm to 600 μm, and may preferably be in the range of 500 nm to 100 μm or 100 μm to 400 μm.

In certain embodiments, the three-dimensional culture carrier has a void ratio of 60% or more, preferably 70% or more, more preferably 75% or more, and particularly preferably 80% or more.

In another embodiment, the average area of the openings of the three-dimensional culture carrier is 0.1 to 100 $\mu m^2$, preferably 0.2 to 60 $\mu m^2$, and more preferably 0.5 to 30 $\mu m^2$. When the openings is a pore, the openings area corresponds to the pore area.

The three-dimensional culture carrier has a structure in which fibers are three-dimensionally integrated, in other words, fibers are stacked in the three-dimensional direction. The fibers may be arranged regularly or irregularly, and the fibers may or may not be connected to each other.

The three-dimensional culture carrier is not limited as long as the cell contact surface thereof has a three-dimensional structure formed of fibers. The three-dimensional culture carrier may also include a portion to which cells do not adhere, typically a base member, beneath the fibrous three-dimensional structure. The structure of the base member may be any structure as long as the base member can support the three-dimensional structure described above. For example, the base member can be nonwoven fabric, knit fabric, textile fabric, porous scaffold material, and the like. The three-dimensional culture carrier used as a support is not limited as long as the three-dimensional culture carrier is made of a biocompatible material and has a sheet-like shape. The shape, size, and thickness of the three-dimensional culture carrier are not limited as long as the three-dimensional culture carrier can be easily handled in cell culture and the subsequent transplantation into a living body. However, for example, a three-dimensional culture carrier formed integrally with a cell culture vessel or the like that cannot be used for transplantation into a living body is not included.

The cell contact surface of the three-dimensional culture carrier is not limited as long as the main part thereof has a three-dimensional structure formed of fibers, specifically, as long as 50% or more of the area of the culture carrier is occupied by a portion having the three-dimensional structure formed of fibers when the culture carrier is observed from the cell contact surface side, typically, from the upper side. Thus, the three-dimensional culture carrier can include, in a part of the cell contact surface, a portion that does not have the "three-dimensional structure formed of fibers", for example, a flat film-like portion without a three-dimensional structure or the like. The area of the portion on the contact surface may be in the range of 50% or less, preferably in the range of 40% or less, and more preferably in the range of 30% or less.

Examples of the three-dimensional culture carrier that can be used in the present invention include VECELL (registered trademark) (polytetrafluoroethylene, average fiber diameter: <1 μm, average pore area: 1 to 20 $\mu m^2$, average diameter of openings: 20 to 100 µm, void ratio: 80 to 90%) available from Vessel Inc.; Cellbed (registered trademark) (high-purity silica fibers, average fiber diameter: 1 µm, mean flow pore size: 7 to 8 µm, void ratio: >95%) available from Japan Vilene Company Ltd.; 3D Insert-PS series (polystyrene fibers, average fiber diameter: PS-200 is 150 µm or below and PS-400 is 300 µm or below, average diameter of openings: PS-200 is 200 µm and PS 400 is 400 µm) available from 3D Biotek, LLC; the cell culture substrate described in WO2014/196549 pamphlet; the cell culture substrate (biodegradable polymer, average fiber diameter 50 nm to 5 µm) described in WO2016/068266 and U.S. Patent Application Publication No. 2017/319747 corresponding thereto; the cell culture substrate (polyglycolic acid, average fiber diameter: 345±91 nm, average pore area: 0.68±0.02 µm$^2$, average diameter of openings calculated from average pore area: 0.93 µm ((0.68 µm$^2$/π)$^{1/2}$)×2)) described in Liu L, Kamei K et al., Biomaterials 124 (2017) 47-54; and commercially available tissue reinforcing members such as NEOVEIL and NEOVEIL nano (polyglycolic acid, Gunze Co., Ltd.). Each of the above references is incorporated herein its entirety by reference.

The cell sheet according to the present invention can be applied locally in vivo, by transplanting the cell sheet on the site where a disease is developing, the site where a disease may develop, or the site causing a disease, or the vicinity of these sites in a living body, thereby the disease that can be effectively treated and/or prevented by the cell transplantation therapy using MSCs can be treated and/or prevented. For example, such diseases include diabetes and the complication thereof; cerebrovascular disease; cerebral degeneration disease; demyelinating disease; functional and seizure disorders; dementing disorder; peripheral nerve disease; cardiovascular disease; autoimmune disease; liver, biliary tract, and pancreas diseases; gastric and duodenal diseases; small and large intestine and colon diseases; thyroid disease; hematologic and hematopoietic diseases; lung disease; acute kidney injury and chronic kidney disease; eye disease; skin disease; muscular and bone diseases; trauma; and graft-versus-host disease (GVHD). Specifically, the disease that can be treated and/or prevented by locally applying the cell sheet include type 1 diabetes, type 2 diabetes, and the complication thereof such as diabetic nephropathy, diabetic retinopathy, diabetic neuropathy, and diabetic gangrene; cerebrovascular disease such as stroke (cerebral infarction and cerebral hemorrhage); cerebral degeneration disease such as Parkinson's disease, Huntington's disease, corticobasal degeneration, multiple system atrophy, spinocerebellar degeneration, and amyotrophic lateral sclerosis (ALS); demyelinating disease such as multiple sclerosis, acute disseminated encephalomyelitis, and neuromyelitis optical; functional and seizure disorders such as epilepsy and cerebral palsy; dementing disorder such as vascular dementia, Alzheimer's disease, Lewy body dementia, frontotemporal dementia, and diabetes-related dementia; peripheral nerve disease such as Guillain-Barre syndrome, peripheral neuropathy, facial palsy, trigeminal neuralgia, dysuria, erectile dysfunction, and autonomic imbalance; cardiovascular disease such as myocardial infarction, angina pectoris, arteriosclerosis obliterans, and cardiomyopathy; autoimmune disease such as rheumatoid arthritis, systemic lupus erythematosus, Sjogren's syndrome, polymyositis, dermatomyositis, scleroderma, mixed connective-tissue disease, polymyalgia rheumatica, eosinophilia, Behcet's disease, sarcoidosis, Still's disease, spondylarthritis, and Kawasaki disease; liver, biliary tract, and pancreas diseases such as acute and chronic hepatitis, hepatic cirrhosis, autoimmune hepatitis, primary biliary cirrhosis, primary sclerosing cholangitis, acute and chronic pancreatitis, and autoimmune pancreatitis; gastric and duodenal diseases such as acute and chronic gastritis, gastric and duodenal ulcers; small and large intestine and colon diseases such as Crohn's disease, ulcerative colitis, ischemic colitis, and irritable bowel syndrome; thyroid disease such as Basedow's disease, and acute and chronic thyroiditis; hematologic and hematopoietic diseases such as autoimmune hemolytic anemia, polycythemia vera, and idiopathic thrombocytopenic purpura; lung disease such as chronic obstructive pulmonary disease, interstitial pneumonitis, pulmonary fibrosis, pneumoconiosis, bronchial asthma, eosinophilic pneumonia, and acute respiratory distress syndrome (ARDS); acute kidney injury such as acute kidney injury with fluid loss or ischemia, anti-neutrophil cytoplasmic antibody (ANCA)-associated nephritis, microscopic polyangiitis, granulomatosis with polyangiitis, eosinophilic granulomatosis with polyangiitis, malignant hypertension, cryoglobulinemia, postinfectious glomerulonephritis, immunoglobulin A (IgA) nephropathy, acute interstitial nephritis, drug-induced nephropathy, myeloma cast nephropathy, gouty nephropathy, rhabdomyolysis, and acute kidney tubular necrosis; chronic kidney disease such as membranous nephropathy, membranoproliferative glomerulonephritis, minimal change nephrotic syndrome, focal glomerular sclerosis, lupus nephritis, amyloidosis, nephrosclerosis, purpura nephritis, immunoglobulin G4 (IgG4)-related kidney disease, Sjogren's syndrome, scleroderma kidney, chronic interstitial nephritis, and polycystic kidney disease; eye disease such as macular degeneration, optic neuritis, and uveitis; skin disease such as atopic dermatitis, bullous disease, and Stevens-Johnson syndrome; muscular and bone diseases such as myasthenia gravis, muscular dystrophy, coxarthrosis, femur head necrosis, osteoporosis, and carpal tunnel syndrome; trauma such as spinal cord injury and brain contusion; wound such as pressure ulcers; oral ulcers; graft-versus-host disease (GVHD); anastomotic leakage; and damage to organs. The disease to which the cell sheet according to the present invention is applied, is preferably diabetic nephropathy, acute kidney injury, chronic kidney disease, diabetic retinopathy, diabetic neuropathy, diabetic gangrene, Alzheimer's disease, diabetes-related dementia, rheumatoid arthritis, polymyositis, and wound.

The treatment and/or prevention used herein encompass all types of medically acceptable therapeutic and/or preventive interventions intended to cure, temporarily ameliorate, or prevent a disease or a symptom, or the like. In other words, the treatment and/or prevention of a disease or a symptom encompass medically acceptable interventions for various purposes including delaying or stopping the progression of a disease or a symptom, regression or disappearance of a lesion, preventing the onset or avoiding the recurrence, and the like.

An effective amount of the cell sheet according to the present invention is locally applied to a subject. The "effective amount" means an amount effective for treating and/or preventing a disease. The effective amount is appropriately adjusted depending on the type of disease, an organ or tissue to which the cell sheet is locally applied, the severity of a symptom, a patient, and other medical factors. In a preferred embodiment, the effective amount of the cell sheet contains $10^2$ MSCs to $10^9$ MSCs, and preferably $10^4$ MSCs to $10^6$ MSCs, per kg body weight of an individual to which the cell sheet is applied.

A preferred embodiment of the cell sheet according to the present invention is a cell sheet for use in treating kidney disease, that contains MSCs having an average cell density ranging from $1.0 \times 10^3$ cells/cm$^2$ to $3.0 \times 10^4$ cells/cm$^2$, preferably from $2.0 \times 10^3$ cells/cm$^2$ to $3.0 \times 10^4$ cells/cm$^2$, more preferably from $2.0 \times 10^3$ cells/cm$^2$ to $2.0 \times 10^4$ cells/cm$^2$, further preferably from $2.0 \times 10^3$ cells/cm$^2$ to $1.8 \times 10^4$ cells/cm$^2$, still preferably from $3.0 \times 10^3$ cells/cm$^2$ to $1.6 \times 10^4$ cells/cm$^2$, still more preferably from $3.0 \times 10^3$ cells/cm$^2$ to $1.0 \times 10^4$ cells/cm$^2$, and particularly preferably from $3.0 \times 10^3$ cells/cm$^2$ to $8.0 \times 10^3$ cells/cm$^2$ on the surface thereof. In this aspect, the cell sheet is transplanted into the kidney, preferably under the kidney fibrous capsule in an adhesive manner. In this process, it is preferable to separate Gerota's fascia and fat capsule detached from the kidney away from the kidney parenchyma as much as possible. By transplanting the cell sheet into the kidney of a kidney disease patient, it is possible to suppress or inhibit the progression of kidney disease and symptoms associated therewith, and further improve the disease and symptoms. For example, by transplanting the cell sheet under the kidney fibrous capsule of a patient with severe chronic kidney disease, in particular, that has reached end-stage kidney failure, it is possible to suppress the progression of renal impairment and reduce mortality.

Another preferred aspect of the cell sheet according to the present invention is a cell sheet for use in treating brain injury or neurodegenerative disease, that contains MSCs having an average cell density ranging from $0.5 \times 10^3$ cells/cm$^2$ to $1.5 \times 10^4$ cells/cm$^2$, preferably from $1.0 \times 10^3$ cells/cm$^2$ to $1.5 \times 10^4$ cells/cm$^2$, and more preferably from $1.8 \times 10^3$ cells/cm$^2$ to $0.5 \times 10^4$ cells/cm$^2$ on the surface thereof. In this aspect, the cell sheet is transplanted into a site of brain injury, a site of brain degeneration, or the vicinity of these sites, in an adhesive manner. By transplanting the cell sheet into the brain of a patient with brain injury or neurodegenerative disease, it is possible to suppress or inhibit the progression of brain injury, neurodegenerative disease, and the symptoms associated therewith, and further improve the disease and symptoms. For example, it is possible to improve cognitive function, by transplanting the cell sheet into the degenerative site of neurodegenerative disease.

In the cell sheet according to the present invention, the average cell density of MSCs is greatly lower than that of the conventional cell sheet containing MSCs. As will be described in the following examples, the inventors of the present invention have found that the therapeutic effect of individual MSCs can be markedly increased, by culturing the MSCs on a cell culture carrier having a three-dimensional structure formed of fibers at low cell density. Surprisingly, the therapeutic effect of the cell sheet containing MSCs cultured at low density are greater than those of the conventional cell sheet containing MSCs as a whole, even though the cell number of MSCs of the cell sheet is greatly lower than that of the conventional cell sheet containing MSCs.

A method for treating and/or preventing a disease that can be effectively treated and/or prevented by a cell transplantation therapy using MSCs, including locally applying an effective amount of the cell sheet according to the present invention to a subject in need thereof, is also encompassed by the present invention, as another aspect. The meanings of terms in this aspect are as described above.

Method for Producing Cell Sheet

The cell sheet according to the present invention can be produced by a method including a step of seeding MSCs, for example, MSCs separated from a subject with a disease, on a cell culture carrier having a three-dimensional structure formed of fibers, at a cell number of $3.0 \times 10^5$ cells/cm$^2$ or less; and a step of culturing the MSCs and thereby preparing a cell sheet containing the MSCs having an average cell density of $3.0 \times 10^4$ cells/cm$^2$ or less. The method is another aspect of the present invention.

The terms "subject" and the "MSCs separated from a subject with a disease" are interpreted to have the same meanings as those described in WO2015/137419 pamphlet that is Patent Literature 1, and U.S. Patent Application Publication No. 2017/0071984 corresponding thereto. These documents are incorporated herein by reference in their entirety. The meanings of the terms in these references and the present specification will be outlined below.

The "subject" means any animal with MSCs. For example, the subject is preferably a mammalian individual including primates such as humans and chimpanzees; rodents such as mice, rats, guinea pigs, and hamsters; Artiodactyla such as cows, goats, sheep, and pigs; Perissodactyla such as horses; and individuals of rabbits, dogs, cats, and the like. More preferably, the subject is a human individual.

In the present invention, MSCs used for producing the cell sheet may be MSCs separated from a healthy subject, or MSCs separated from a subject with a disease. MSCs used in the present invention may also be MSCs obtained by inducing differentiation from pluripotent stem cells such as induced pluripotent stem cells (iPS cells), embryonic stem cells (ES cells), embryonal carcinoma cells (EC cells), and embryonic germ cells (EG cells).

As described in Patent Literature 1, it is known that the therapeutic effect of MSCs in subjects with certain types of diseases and aged subjects is lower than that in healthy people, and therefore high therapeutic effects cannot be expected by simply transplanting autologous MSCs as they are into these subjects. In the production method according to the present invention, it is possible to enhance the therapeutic effect of individual MSCs by culturing the MSCs on a three-dimensional culture carrier at low density. Thus, it is possible to produce a cell sheet with high therapeutic effect even when MSCs with low therapeutic effect such as the above are used as a source. The diseases affecting subjects having MSCs with low therapeutic effect are chronic diseases, and examples of such diseases are described in Patent Literature 1 as diseases in which MSCs become abnormal.

When safety in the subsequent cell transplantation therapy is taken into consideration, it is preferable to collect MSCs from an individual of the same species or a related species of an individual to which the MSCs are to be applied. For example, when MSCs are transplanted into a human individual, MSCs collected from human, which is the same species, are preferably used, and MSCs collected from the same human individual to which the cells are to be applied, in other words, autologous MSCs are more preferably used.

The MSCs used for producing a cell sheet in the present invention can be collected from a sample such as bone marrow fluid, adipose tissue, fetal appendage tissue, and dental pulp from a subject, by using a general method. For example, when bone marrow fluid is used as the sample, it is possible to separate the MSCs by using a known method such as a density gradient centrifugation method and bone marrow seeding. In one preferred embodiment of the present invention, the MSCs are MSCs derived from bone marrow or adipose tissue.

The production method according to the present invention includes a step of seeding MSCs on a cell culture carrier having a three-dimensional structure formed of fibers, at a cell number of $3.0 \times 10^5$ cells/cm$^2$ or less. This process can be performed by placing the sheet-shaped cell culture carrier having the three-dimensional structure formed of fibers described above in a general cell culture vessel, adding a culture medium, immersing the cell culture carrier, and seeding the MSCs thereon with adjusted cell number.

The size of the bottom of the cell culture vessel is not limited as long as the three-dimensional culture carrier can be placed thereon in an expanded state. It is preferable that the most of the bottom is covered with the three-dimensional culture carrier, when the three-dimensional culture carrier is placed thereon in an expanded state. In certain embodiments, the bottom of the cell culture vessel has the same shape as that of the three-dimensional culture carrier, or has a shape such that the three-dimensional culture carrier is inscribed in the bottom.

The cell number of MSCs to be seeded is appropriately adjusted according to the average cell density on the cell sheet to be produced. Typically, the cell number of MSCs to be seeded may be in the range of ten to one-tenth times of the average cell density on the cell sheet to be produced, and may preferably be in the range of ten to one times. For example, when preparing a cell sheet having an average cell density of $3.0 \times 10^4$ cells/cm$^2$, the cell number of MSCs to be seed ranges from $3.0 \times 10^5$ cells/cm$^2$ to $3.0 \times 10^3$ cells/cm$^2$. When preparing a cell sheet having an average cell density of $2.0 \times 10^4$ cells/cm$^2$, the cell number of MSCs to be seeded ranges from $2.0 \times 10^5$ cells/cm$^2$ to $2.0 \times 10^3$ cells/cm$^2$. When preparing a cell sheet having an average cell density of $1.0 \times 10^4$ cells/cm$^2$, the cell number of MSCs to be seeded ranges from $1.0 \times 10^5$ cells/cm$^2$ to $1.0 \times 10^3$ cells/cm$^2$. When preparing a cell sheet having an average cell density of $5.0 \times 10^3$ cells/cm$^2$, the cell number of MSCs to be seeded ranges from $5.0 \times 10^4$ cells/cm$^2$ to $5.0 \times 10^2$ cells/cm$^2$. When preparing a cell sheet having an average cell density of $1.0 \times 10^3$ cells/cm$^2$, the cell number of MSCs to be seeded ranges from $1.0 \times 10^4$ cells/cm$^2$ to $1.0 \times 10^2$ cells/cm$^2$. When preparing a cell sheet having an average cell density of $0.5 \times 10^3$ cells/cm$^2$, the cell number of MSCs to be seeded ranges from $0.5 \times 10^4$ cells/cm$^2$ to $0.5 \times 10^2$ cells/cm$^2$.

The number of cells to be seeded described above is a numerical value per area of the three-dimensional culture carrier. The actual number of cells to be seeded can be obtained by dividing the bottom area of the cell culture vessel by the area of the three-dimensional culture carrier, and multiplying the calculated value.

The culture medium may be a culture medium generally used for culturing MSCs such as α-MEM and DMEM. The culture medium may contain various components, such as serum components, required for MSC proliferation.

The production method according to the present invention includes a step of culturing the MSCs on a culture carrier having a three-dimensional structure formed of fibers, and thereby preparing a cell sheet containing the MSCs having an average cell density of $3.0 \times 10^4$ cells/cm$^2$ or less.

The MSCs are cultured on the three-dimensional culture carrier for 24 hours to 144 hours, preferably for 24 hours to 96 hours, and more preferably for 48 hours to 96 hours. The culture temperature and gas concentration in the culture process may be in the range of temperature and gas concentration generally used for culturing MSCs. For example, the temperature is 25° C. to 37° C., preferably 30° C. to 37° C., and more preferably 37° C. For example, the oxygen concentration is 2% to 30%, and preferably 2% to 20%. It is possible to prepare a cell sheet having an intended average cell density, by adjusting the number of cells to be seeded on the culture carrier in the range described above, and adjusting the culture conditions such as culture time and temperature as necessary.

The cell sheet produced by the method described above may be used such that the three-dimensional culture carrier remains contained in the cell sheet as a support. If the cell sheet can be detached from the three-dimensional culture carrier, the cell sheet detached therefrom may be used, or, as necessary, a combination of the cell sheet detached from the three-dimensional culture carrier with another support may be used. The culture carrier from which the cell sheet can be detached includes a cell culture carrier having a three-dimensional structure formed of fibers, being surface-coated with a polymer that changes its molecular structure in response to stimuli such as temperature, pH and light. Example of the polymer include poly (N-isopropyl acrylamide).

When the cell sheet does not contain a support, in other words, when the cell sheet consists of MSCs adhering to each other, the culture carrier is not necessarily formed in a sheet shape. In this case, the shape of the three-dimensional culture carrier is not limited as long as cells can come into contact with the three-dimensional structure formed of fibers in culture. The three-dimensional culture carrier may be formed in an insertable shape such that the culture carrier is installed in the cell culture vessel to be used. Alternatively, the three-dimensional culture carrier may be formed in a shape such that the three-dimensional structure is formed integrally on the inner surface of the cell culture vessel such as on the bottom of a well.

The MSCs on the cell sheet may be maintained in an undifferentiated state, or may be differentiated into desired cells. The MSCs may be maintained in an undifferentiated state, by culturing the MSCs in a culture medium suitable for maintaining the undifferentiated state, such as HyClone AdvanceSTEM Mesenchymal Stem Cell Expansion Kit (Thermo Fisher Scientific), MesenCult (trademark) MSC Basal Medium (Stemcell Technology), Stromal Cellutions (trademark) Media (DV Biologics), MSC culture medium kit (MSCGM BulletKit, Lonza), or the like. The MSCs may be differentiated using a generally known method such as culturing MSCs in a differentiation-inducing culture medium added with a factor for inducing MSCs to differentiate into desired cells. For example, to differentiate MSCs into osteoblasts, bone morphogenetic protein (BMP) 4, BMP 2, or the like is used as a differentiation-inducing factor. To differentiate MSCs into adipocytes, dexamethasone, 3-isobutyl-1 methylxanthine, insulin, or the like is used as a differentiation-inducing factor.

Using Activator in Producing Method

To enhance the therapeutic effect of a cell sheet to be prepared, in the production method according to the present invention, it is preferable to culture MSCs using a culture medium containing an activator that contains an extract from a mammalian fetal appendage as an active ingredient.

An example of the "extract from a mammalian fetal appendage" that can be used in the present invention is the extract described in WO2015/137419 that is Patent Literature 1, and U.S. Patent Application Publication No. 2017/0071984 corresponding thereto, the contents of which are incorporated herein by reference in their entirety. The extract is an extract prepared from a fetal appendage expelled from mother's body or removed from mother's body by cesarean section, as the afterbirth after the fetus of a mammal, preferably a human, is delivered. The fetal appendage is preferably umbilical cord tissue, placental tissue, or placental membrane. The extract is prepared by immersing the fetal appendage as it is or after cutting or crushing, in an extraction medium such as distilled water, a physiological saline solution, a phosphate-buffered physiological saline solution, and a medium commonly used for cell culture. It is particularly preferable that the extract is free from a cell having proliferation potency derived from the donor mammal. Specific extraction operations and conditions may comply with the operations and conditions described in Patent Literature 1.

Another example of the "extract from a mammalian fetal appendage" may be an extract prepared by subjecting the fetal appendage to a treatment generally used by those skilled in the art in preparing a bioactive substance from a fetal appendage, typically, from a placenta. Examples of the treatment generally used by those skilled in the art include hydrolysis using acids, enzymes, or the like. Examples of such extracts include placental preparation "Melsmon" that is a human placental acid hydrolysis product commercially available from Melsmon Pharmaceutical Co., Ltd.; human placental preparation "Laennec" commercially available from Japan Bio Products Co., Ltd.; and other commercial placental preparations and various commercial products called placenta extracts.

The "activator that contains an extract from a mammalian fetal appendage as an active ingredient" in the present invention is an agent that contains the extract described above as an active ingredient, and that increases the therapeutic effect of MSCs. Hereinafter, the agent will be referred to as an "activator".

The concentration of the activator in the culture medium used for culture may be sufficient at the final concentration of 0.01 µg/mL to 500 µg/mL in terms of protein. However, the concentration of the activator is preferably from 0.02 µg/mL to 300 µg/mL, and more preferably from 0.04 µg/mL to 100 µg/mL. In certain embodiments, the concentration of the activator may be from 0.05 µg/mL to 10 µg/mL.

Hereinafter, the present invention will be described in more detail with reference to the following examples. The present invention is not limited to these examples.

EXAMPLES

Reference Example 1 MSC Culture on Three-Dimensional Culture Carrier in Presence of Activator 1. Preparation of Activator The activator was prepared from human placental tissue according to the description in Patent Literature 1. In Brief, finely stripped human placental tissue was placed in a serum-free culture medium (alpha-MEM) at a ratio of 100 mL to 50 g wet weight, followed by shaking at 4° C. for 72 hours. The supernatant was collected by centrifugation, and an activator, which is placental tissue extract, was obtained.

2. Culturing of MSCs

Bone marrow-derived MSCs collected from a coxarthrosis patient during the joint replacement surgery (OA-MSCs) were cultured in an MSC culture medium (DMEM containing 15% FBS, 1% penicillin, 1% streptomycin, 4,500 mg/L glucose and L-glutamine) without an activator. The cells were then collected, and seeded onto cell culture carriers having a three-dimensional structure formed of fibers, namely, Preset VECELL 6-well (registered trademark) (Vessel Inc.) at $8 \times 10^4$ cells/well, Cellbed 24-well (registered trademark) (Japan Vilene Company, Ltd.) at $2 \times 10^4$ cells/well, and 3-D insert PS-200 12-well and 3D-insert PS-400 12-well (3D Biotek, LLC) each at $3.8 \times 10^4$ cells/well. The cells were also seeded onto a cell culture substrate A (average fiber diameter 0.1 to 0.5 µm, void ratio 70% or less, average pore area 0.2 µm$^2$, 24-well) that is a culture carrier of the comparative example, at $2 \times 10^4$ cells/well. The cells were then cultured at 37° C. for 72 hours by using the MSC culture medium without an activator. The substrate A partially has a three-dimensional structure formed of fibers, however about 50% of the cell contact surface of the substrate A is occupied by a flat film-like portion that does not have a three-dimensional structure. After removing the culture medium, the MSC culture medium with 10 µg/mL, 1 µg/mL, or 0.1 µg/mL of the above-described activator in terms of protein, or the MSC culture medium without an activator was each added to Preset VECELL 6-well by 2 mL; to Cellbed 24-well and the substrate A by 0.6 mL; and to 3D-insert PS-200 12-well and 3D-insert PS-400 12-well by 1 mL. The cells were then cultured at 37° C. for 4 days. The culture was performed once to three times, then the cells were collected, and OA-MSCs at passages 1 to 3 were prepared.

Further, OA-MSCs cultured in the MSC culture medium without an activator were seeded at $6 \times 10^4$ cells/well onto Corning (registered trademark) Costar (registered trademark) cell culture 6-well plate (Thermo Fisher Scientific Inc.) that is a flat two-dimensional cell culture carrier. The cells were then cultured in the presence of 100 µg/mL activator. By repeating the above described culture once again, control OA-MSCs at passage 2 were prepared.

Example 1 Preparation of Cell Sheets

OA-MSCs were cultured in an MSC culture medium (DMEM containing 15% FBS, 1% penicillin, 1% streptomycin, 4500 mg/L glucose and L-glutamine) without an activator. $8 \times 10^4$ cells of the collected MSCs were seeded on a two-dimensional culture carrier (Corning (registered trademark) Costar (registered trademark) cell culture 6-well plate, Thermo Fisher Scientific Inc.) in which a piece of 2.5 cm×2.5 cm cell culture substrate B was placed. Then, 2 mL of the MSC culture medium containing 1 µg/mL activator was added, and cultured at 37° C. for 72 hours to prepare an OA-MSC sheet at passage 1. The MSC sheet prepared by this method contains about 8,500 cells/cm$^2$ MSCs. The cell culture substrate B is a three-dimensional culture carrier manufactured by the method described in WO2016/068266 and in Liu L, Kamei K et al., Biomaterials 124 (2017) 47-54. The cell culture substrate B contains nanofibers made of polyglycolic acid on a base member made of polyglycolic acid.

Example 2 MSC Gene Expression Analysis

The MSCs prepared in Reference Example 1 and Example 1 were collected, and total RNAs were extracted using Tri Reagent (Molecular Research Center, Inc.). Clone DNAs were synthesized by reverse transcription reaction, and real-time PCR was performed on OCT4, Nanog, SOX2, DNMT1, TERT, IL-6, IDO, TSG-6, p16$^{ink4a}$, p21, p53, α-SMA, and 18sRNA, using primer sets having the base sequences listed in Table 1.

In Table 1, (F) refers to a forward primer and (R) refers to a reverse primer.

TABLE 1

| Gene | Base Sequence | SEQ ID NO: |
|---|---|---|
| OCT4(F) | GACAGGGGAGGGGAGGAG | 1 |
| OCT4(R) | CTTCCCTCCAACCAGTTGCCC | 2 |
| NANOG(F) | TGGACACTGGCTGAATCCTTC | 3 |
| NANOG(R) | CGTTGATTAGGCTCCAACCAT | 4 |
| SOX2(F) | GGGAAATGGGAGGGGTGCAA | 5 |
| SOX2(R) | TTGCGTGAGTGTGGATGGGA | 6 |
| DNMT1(F) | CGTAAAGAAGAATTATCCGAGG | 7 |
| DNMT1(R) | GTTTTCTAGACGTCCATTCAC | 8 |
| TERT(F) | CGGAAGAGTGTCTGGAGC | 9 |
| TERT(R) | GGATGAAGCGGAGTCTGGA | 10 |
| IL-6(F) | GATGAGTACAAAAGTCCTGATCCA | 11 |
| IL-6(R) | CTGCAGCCACTGGTTCTGT | 12 |
| IDO(F) | GCATTTTTCAGTGTTCTTCGCATA | 13 |
| IDO(R) | TCATACACCAGACCGTCTGATAGC | 14 |
| TSG-6(F) | CCCATTGTGAAGCAGGGCCCAACTG | 15 |
| TSG-6(R) | GGAAGCTCATCTCCACAGTATCTTCCC | 16 |
| P16INK4a(F) | AGCATGGAGCCTTCGGCTGA | 17 |
| P16INK4a(R) | CCATCATCATGACCTGGATCG | 18 |
| P21(F) | GAGACTCTCAGGGTCGAAAA | 19 |
| P21(R) | TTAGGGCTTCCTCTTGGAGA | 20 |
| TP53(F) | TGACTGTACCACCATCCACTA | 21 |
| TP53(R) | AAACACGCACCTCAAAGC | 22 |
| alpha-SMA(F) | GCAGCCCAGCCAAGCACTGT | 23 |
| alpha-SMA(R) | TGGGAGCATCGTCCCCAGCA | 24 |
| RNA18S(F) | ATCGGGGATTGCAATTATTC | 25 |
| RNA18S(R) | CTCACTAAACCATCCAATCG | 26 |

By using 18sRNA as a housekeeping gene, a ΔΔCT value was calculated on the basis of the control OA-MSCs cultured on the two-dimensional culture carrier in the presence of the activator at 100 μg/mL, and the gene expression profiles were analyzed and clustered. FIG. 1 illustrates the results of the OA-MSCs cultured on Preset VECELL in the presence of 0.1 μg/mL activator (VECELL_0.1), the OA-MSCs cultured on Cellbed in the presence of 0.1, 1, or 10 μg/mL activator (CellBed_0.1, CellBed_1, and CellBed_10), the OA-MSCs cultured on 3D-insert PS-200 in the presence of 0.1 μg/mL activator (3D. insert200_0.1), the OA-MSCs cultured on 3D-insert PS-400 in the presence of 10 μg/mL activator (3D. insert400_10), the OA-MSCs cultured on the substrate A in the presence of 0.1 μg/mL activator (A_0.1), the OA-MSCs cultured on the substrate A in the presence of 1 μg/mL activator (A_1), the OA-MSCs cultured on the substrate B in the presence of 0.1 μg/mL activator (B_0.1), and the control OA-MSCs cultured on the two-dimensional culture carrier in the presence of 100 μg/mL activator (2D_100).

It was observed that the expression levels of DNMT1, Nanog, SOX2, and OCT4 genes known to be involved in stemness, IDO, TSG6, and IL-6 genes known to be involved in immune regulation and anti-inflammatory function, and TERT gene known to be involved in a telomerase activity were increased, while the expression levels of P53 gene known to be involved in cellular senescence and α-SMA gene known to be involved in cytoskeleton were decreased in any of the OA-MSCs cultured on the three-dimensional culture carriers in the presence of an activator, in comparison with 2D_100. OCT4, SOX2, Nanog, DNMT1, IDO, TSG6, IL-6, and TERT are markers the expressions of which are enhanced in MSCs with high therapeutic effect. P53 and α-SMA are markers the expressions of which are suppressed in MSCs with high therapeutic effect. $p16^{ink4a}$ is a positive marker for therapeutic effects indicating a high correlation with OCT4, SOX2, Nanog, IDO, and TSG6, found by the inventors of the present invention. From these results, it was considered that the OA-MSCs cultured on any of the three-dimensional culture carriers had higher therapeutic effect than the OS-MSCs cultured on the two-dimensional culture carrier had. A_1 and A_0.1 showed the gene expression profiles similar to that of 2D_100, therefore the therapeutic effect of the OA-MSCs cultured on the substrate A was inferred to be comparable to that of the OA-MSCs cultured on a general two-dimensional culture carrier.

Example 3 Therapeutic Effect of Cell Sheet on Kidney Disease (Diabetic Nephropathy Accompanied by Acute Kidney Injury)

To 14-month-old male OLETF rats (Hoshino Laboratory Animals) developing diabetic nephropathy, rituximab (Chugai Pharmaceutical Co., Ltd.) in an amount of 5 mg/rat was administered via the tail vein once a day for 4 days. The MSC sheets of Example 1 were transplanted into the kidney of rats administered with rituximab (MSC sheet group, n=6) 10 to 14 days after the first administration of rituximab. Rats subjected to rituximab administration alone were set as Vehicle (vehicle group, n=7). Under isoflurane inhalation anesthesia, skin incision was made under the lowest rib of the rats in a lateral position, and the muscle layer was incised to pull out one of the kidneys from the body. The Gerota's fascia, fat capsule, and fibrous capsule were carefully incised so as not to damage the adrenal gland, removed from the kidney surface, and pulled to the renal hilum. One MSC sheet having a size of 2.5 cm×2.5 cm and another MSC sheet cut into a one-third portion were attached to the kidney so as to cover the whole kidney. The other kidney was also attached with the MSC sheets in the same manner. Blood were collected from the rats on the day of MSC sheet transplantation, and on 3 weeks and 6 weeks after transplantation. Serum creatinine was then measured using an enzymatic method (SRL).

Figure 2:
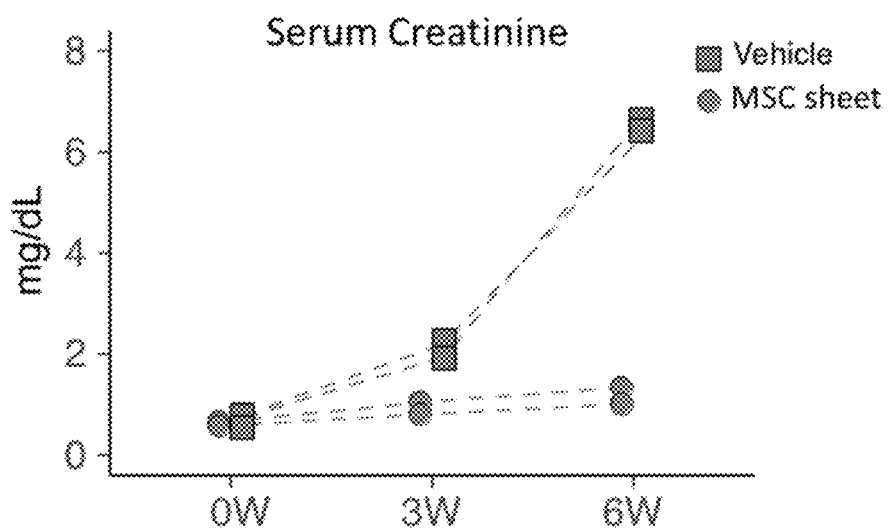
FIG. 2 is a graph illustrating the changes in serum creatinine in diabetic nephropathy rats treated with an anticancer drug, administered with a vehicle or transplanted with a cell sheet.
Figure 3:
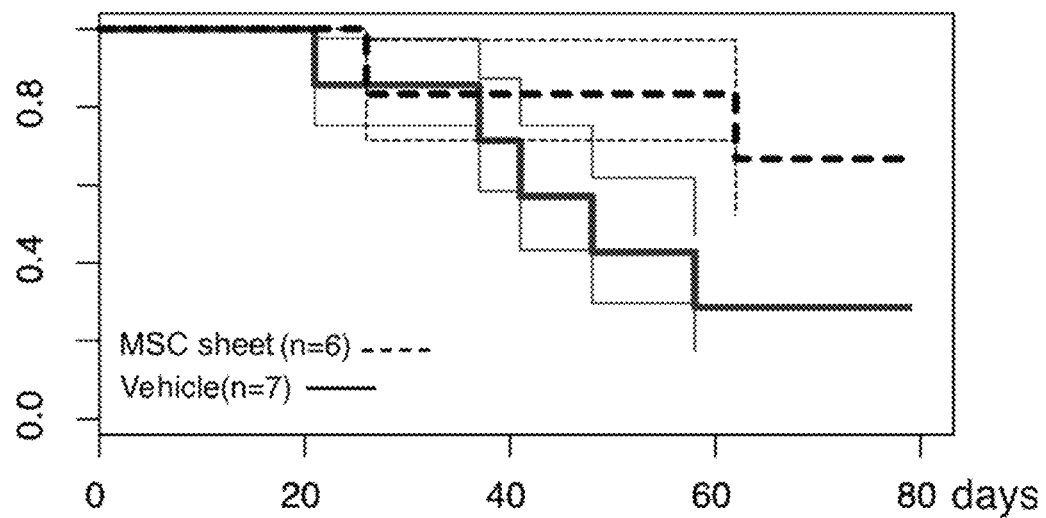
FIG. 3 is a graph illustrating the changes in survival rates of diabetic nephropathy rats treated with an anticancer drug, administered with a vehicle or transplanted with a cell sheet, up to 11 weeks after transplantation. The bold line indicates the average value in each group, and the narrow lines indicate 95% CI (confidence interval) in each group.

FIG. 2 illustrates the changes in serum creatinine in animals that have survived 11 weeks after transplantation (n=2 for both Vehicle group and MSC sheet group). In the Vehicle group, serum creatinine was increased over time, while, in the MSC sheet group, an increase in serum creatinine was not observed. This 6-week maintenance of renal function is equivalent to a 5-year delay in the start of dialysis in humans, demonstrating the high therapeutic effect of the MSC sheet. FIG. 3 illustrates the Kaplan-Meier curves representing the survival rates of rats up to 11 weeks after transplantation. The MSC sheet group showed higher survival rates than those of the Vehicle group.

Figure 4:
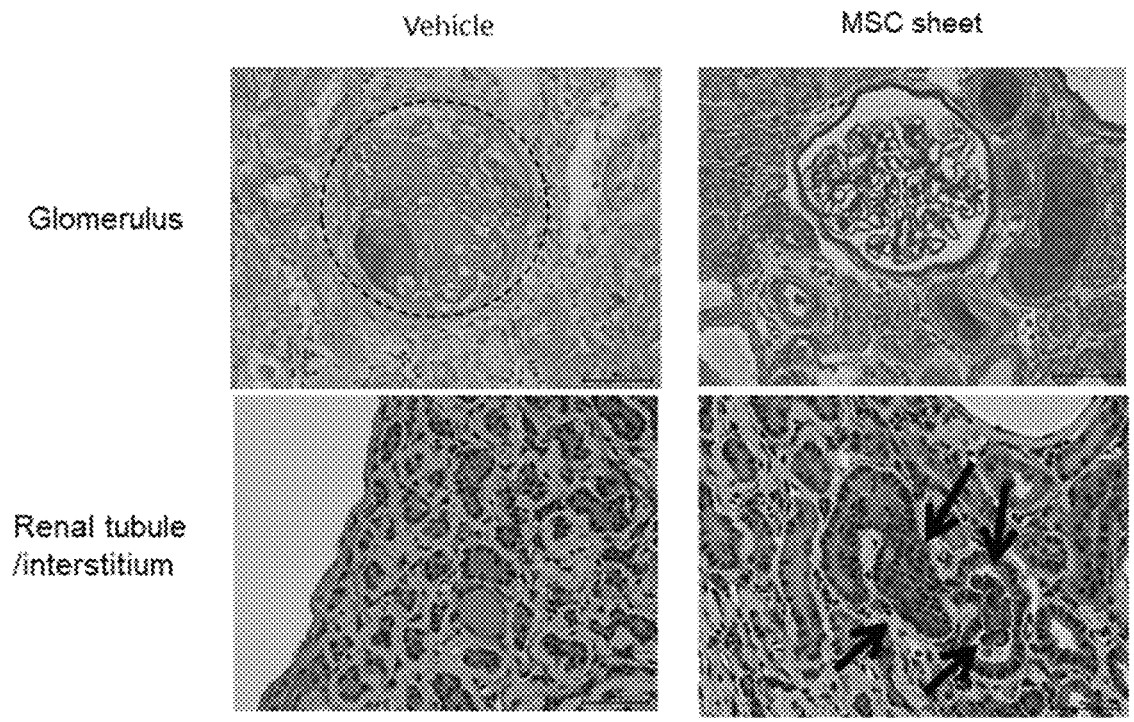
FIG. 4 includes optical microscope observation images of kidney tissue sections of diabetic nephropathy rats treated with an anticancer drug, administered with a vehicle or transplanted with a cell sheet. The upper row images each show a glomerulus, and the lower row images each show renal tubules/interstitium.
Figure 5:
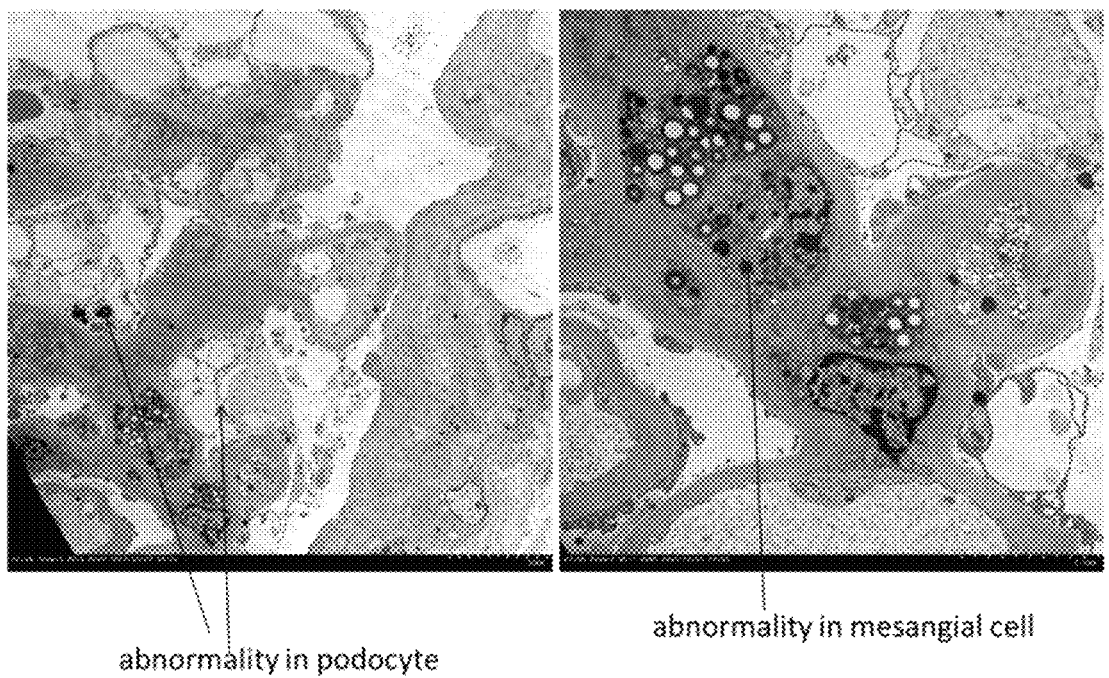
FIG. 5 includes electron microscope observation images of kidney tissue sections of diabetic nephropathy rats treated with an anticancer drug, administered with a vehicle. Each image shows a glomerulus.
Figure 6:
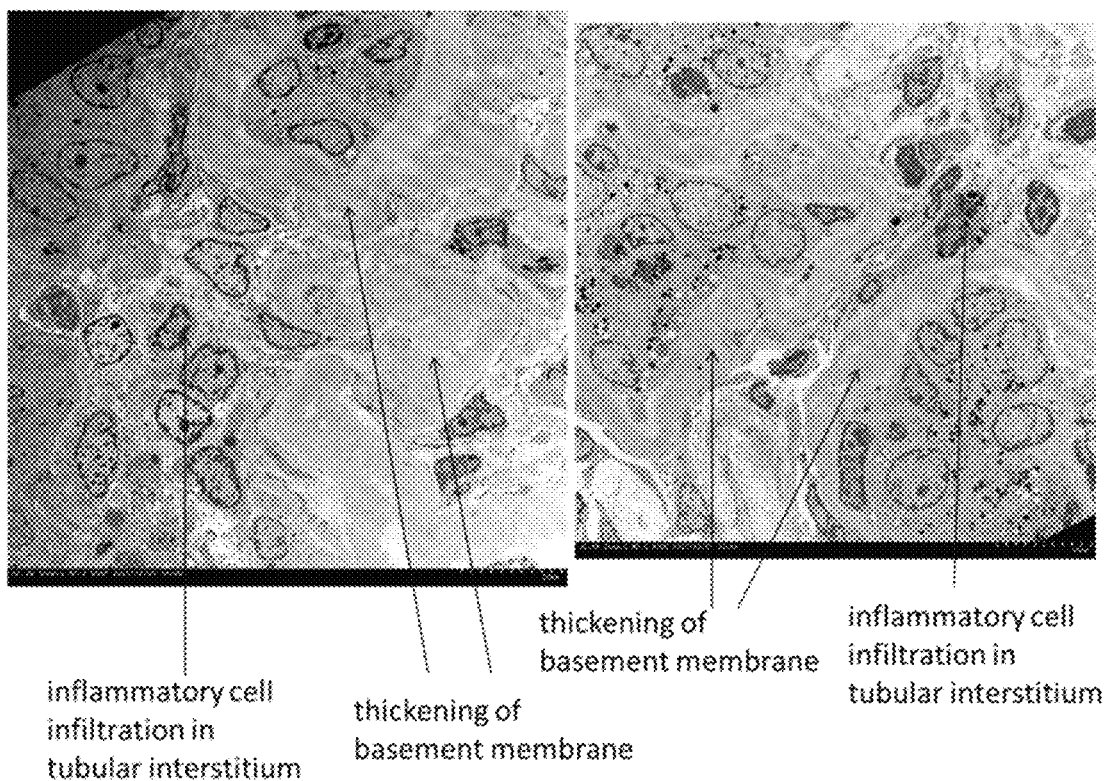
FIG. 6 includes electron microscope observation images of kidney tissue sections of diabetic nephropathy rats treated with an anticancer drug, administered with a vehicle. Each image shows renal tubules.
Figure 7:
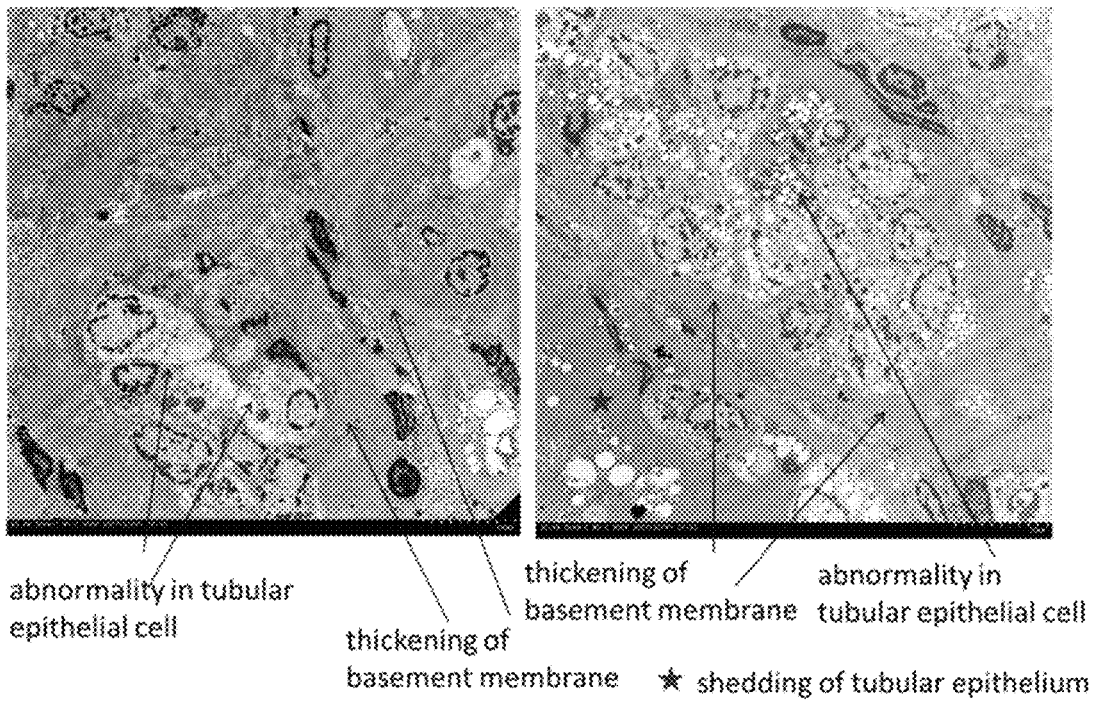
FIG. 7 includes electron microscope observation images of kidney tissue sections of diabetic nephropathy rats treated with an anticancer drug, administered with a vehicle. Each image shows renal tubules.
Figure 8:
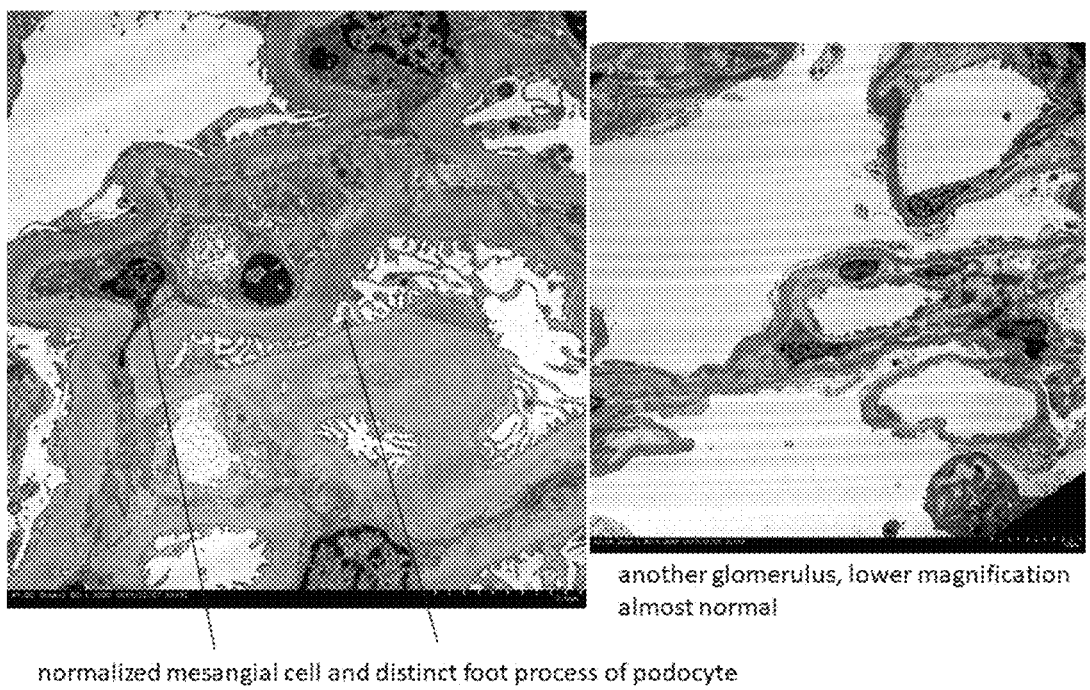
FIG. 8 includes electron microscope observation images of kidney tissue sections of diabetic nephropathy rats treated with an anticancer drug, transplanted with a cell sheet. Each image shows a glomerulus.
Figure 9:
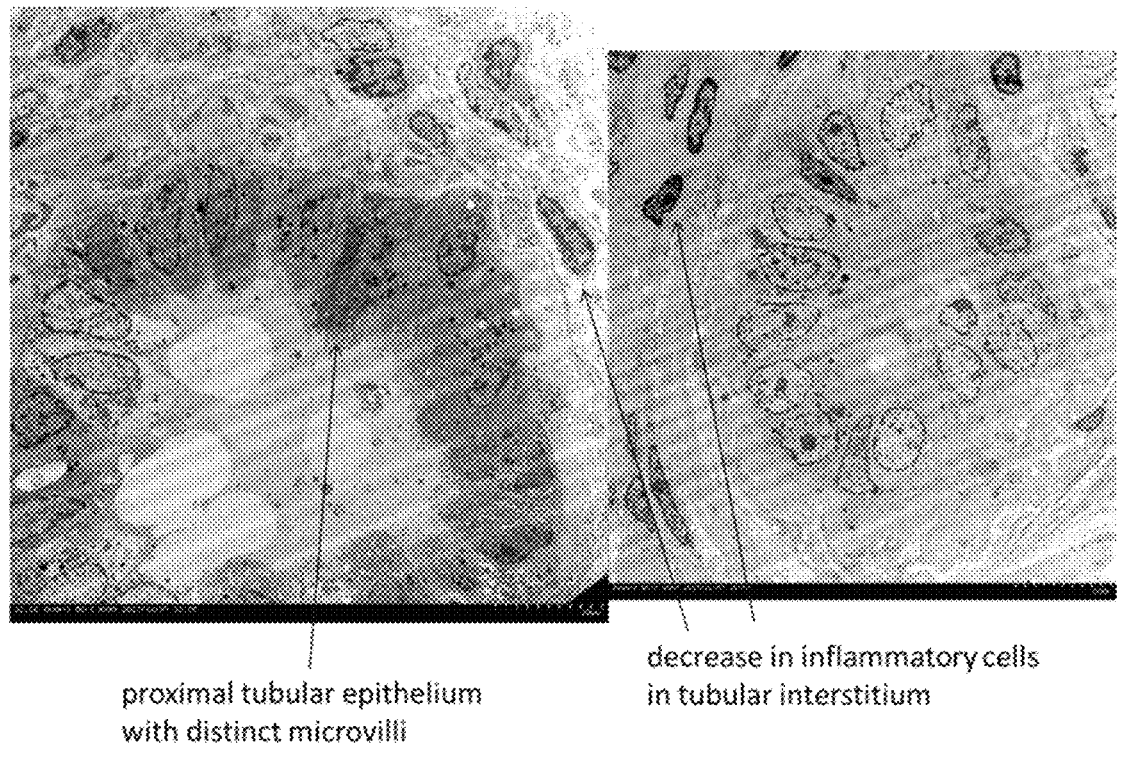
FIG. 9 includes electron microscope observation images of kidney tissue sections of diabetic nephropathy rats treated with an anticancer drug, transplanted with a cell sheet. Each image shows renal tubules.
Figure 10:
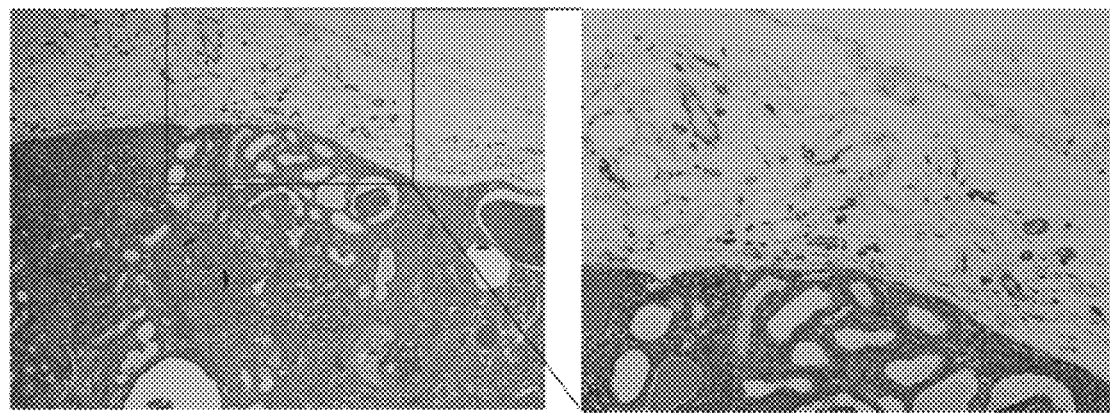
FIG. 10 includes optical microscope observation images of kidney tissue sections of diabetic nephropathy rats treated with an anticancer drug, administered with a vehicle. Each image shows a surface part of kidney.
Figure 11:
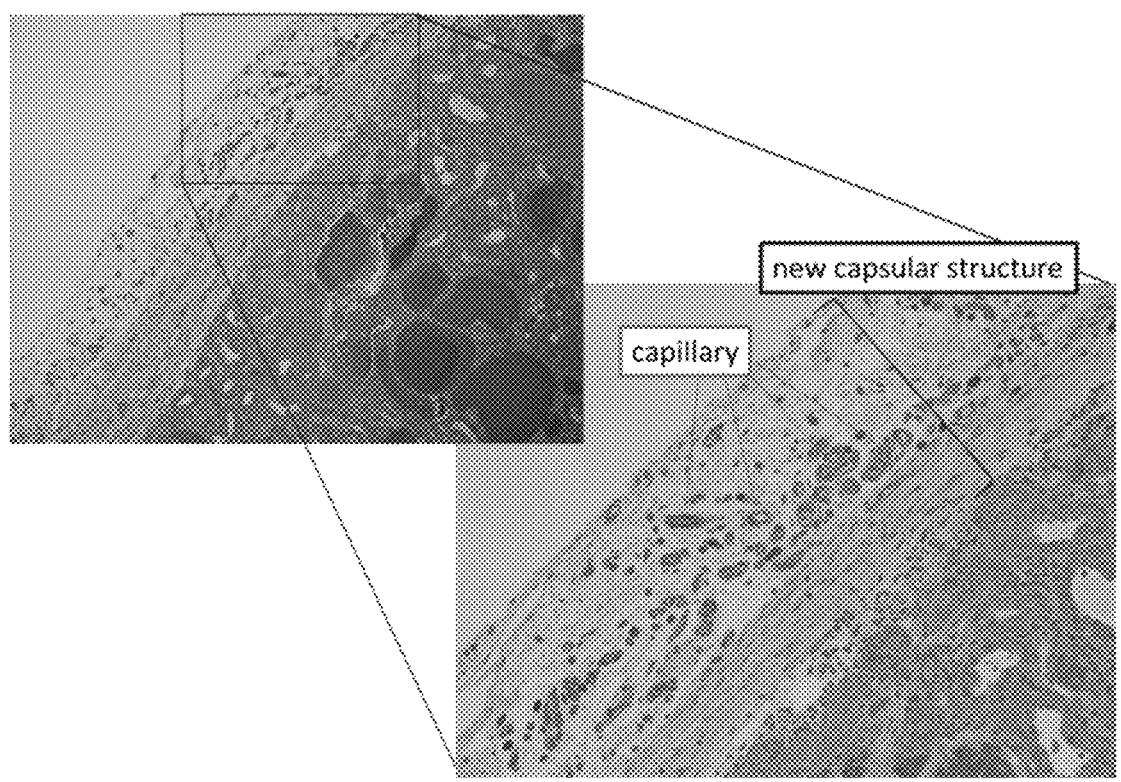
FIG. 11 includes optical microscope observation images of kidney tissue sections of diabetic nephropathy rats treated with an anticancer drug, transplanted with a cell sheet. Each image shows a surface part of kidney.

Further, tissue sections of kidneys removed from animals 11 weeks after transplantation were prepared and the PAS stained samples were observed under an optical microscope and electron microscope. In the Vehicle group, most glomeruli showed sclerosis, and abnormalities were observed in mesangial cells and podocytes (upper left in FIG. 4, and FIG. 5). In the renal tubules, inflammatory cell infiltration in the tubular interstitium, abnormalities in tubular epithelial cells, shedding of tubular epithelium, thickening of the basement membrane, and the like were observed (lower left in FIG. 4, and FIG. 6 and FIG. 7). On the other hand, in the MSC sheet group, normal glomeruli remained (upper right in FIG. 4), and mesangial cells and podocytes were normalized (FIG. 8). Histological findings such as regeneration in tubular epithelial cells (arrows at lower right in FIG. 4), proximal tubular epithelium with distinct microvilli, and a decrease in inflammatory cells in the tubular interstitium (FIG. 9) were also observed, indicating a cure. Furthermore, in the MSC sheet group, the formation of a new capsular structure on the kidney surface and the regeneration of numerous capillaries on the outside thereof were observed (FIG. 10 and FIG. 11).

The rats used in the this study had not only diabetic nephropathy, but also acute kidney disease induced by an anticancer treatment, and thus served as model animals developing severe chronic kidney disease in a uniform degree. The rats showed very severe end-stage kidney injury corresponding to nephropathy stage 4 (kidney failure stage). The cell sheet according to the present invention was found to have an excellent therapeutic effect on such a serious disease.

Example 4 Therapeutic Effect of Cell Sheet on Kidney Disease (Diabetic Nephropathy)

Figure 12:
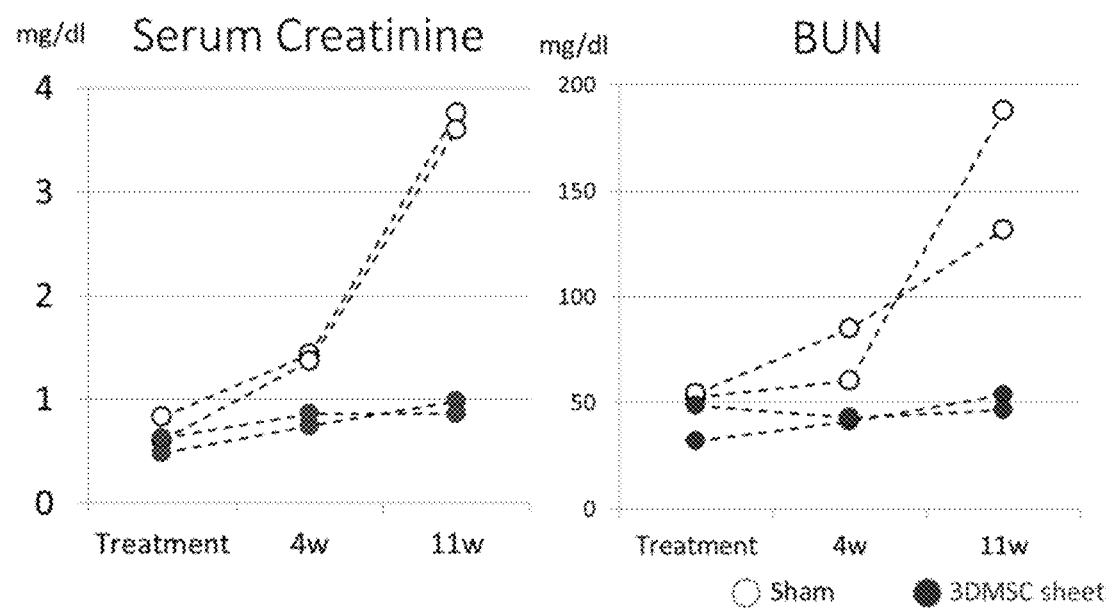
FIG. 12 includes graphs illustrating the changes in serum creatinine and urea nitrogen in diabetic nephropathy rats, transplanted with a cell sheet.

The cell sheets prepared in Example 1 were transplanted into the kidney of 14-months-old male OLETF rats developing diabetic nephropathy under the kidney fibrous capsule (n=2/group), as in Example 3. Rats that underwent a sham operation in which only the dorsal skin and fascia were incised were set as a Sham group. Blood were collected from the rats on the day of MSC sheet transplantation, and on 4 weeks and 11 weeks after transplantation. Serum creatinine was measured using an enzymatic method (SRL), and urea nitrogen (BUN) was measured using a UV method (SRL). FIG. 12 illustrates the changes in serum creatinine and BUN. In the Sham group, serum creatinine and BUN were increased over time, while, in the MSC sheet group, the increase was not observed. The sheet according to the present invention was found to have an excellent therapeutic effect on diabetic nephropathy not accompanied by acute kidney injury.

Example 5 Therapeutic Effect of Cell Sheet on Kidney Disease (Diabetic Nephropathy)

OA-MSCs were cultured in an MSC culture medium (DMEM with 10% FBS, 1% penicillin, 1% streptomycin, 4,500 mg/L glucose and L-glutamine) without an activator. $4 \times 10^3$ cells of the collected MSCs were seeded on a two-dimensional culture carrier (Thermo Scientific (trademark) Nunc (trademark) Lab-Tek™, 8-well, Thermo Fisher Scientific Inc.) in which a piece of 1×0.8 cm NEOVEIL nano (Gunze Co., Ltd.) was placed. Then, 200 μL of the MSC culture medium without an activator was added, and the MSCs were cultured at 37° C. for 24 hours to prepare an OA-MSC sheet at passage 1. The MSC sheet prepared by this method contains 4,781 cells/cm² MSCs (average value of the average cell densities 3,923 to 5,884 cells/cm² of the prepared sheets).

The Gerota's fascia, fat capsule, and fibrous capsule were carefully incised and removed from the kidney surface of the kidneys of 16-week-old male KK-Ay mice developing diabetic nephropathy so as not to damage the adrenal gland. The MSC sheets produced as described above were attached and transplanted to each of both kidneys so as to cover the whole kidney (n=12). As controls, untreated KK-Ay mice (n=9) of the same-week-old developing diabetic nephropathy were prepared. Urine was collected from the mice before MSC sheet transplantation and 4 weeks after transplantation. Urinary albumin was measured using an immunoturbidimetric method (Oriental Yeast Co., Ltd.), and urinary creatinine was measured using an enzyme method (Oriental Yeast Co., Ltd.).

Figure 13:
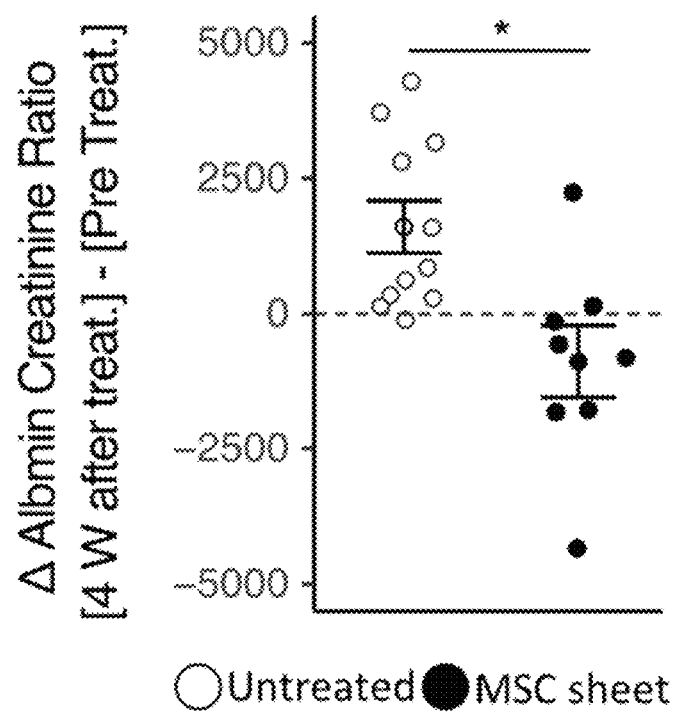
FIG. 13 is a graph illustrating the urinary albumin/creatinine ratio of diabetic nephropathy rats, transplanted with a cell sheet.

FIG. 13 illustrates the difference between urinary albumin/creatinine ratios before MSC sheet transplantation and 4 weeks after MSC sheet transplantation. The urinary albumin/creatinine ratio increased in the untreated group, while rather tended to decrease in the MSC sheet group. Similar to the cell sheet prepared in Example 1, the cell sheet used in this Example was found to have an excellent therapeutic effect on diabetic nephropathy, even though the average cell density on the cell sheet used in this Example is lower than that on the cell sheet prepared in Example 1.

Example 6 Therapeutic Effect of Cell Sheet on Kidney Disease (Acute Kidney Injury Caused by Ischemic Reperfusion)

1. Preparation of Cell Sheet

Following the method described in Example 1, cell sheets containing MSCs with different average cell densities were prepared, by seeding MSCs with the number of cells listed in Table 2 on a piece of 2.5 cm×2.5 cm substrates B, and culturing the MSCs in the MSC culture medium without an activator.

TABLE 2

| Cell Sheet | Number of Seeded Cells (/cm²) | Average Cell Density (/cm²) | |
|---|---|---|---|
| A | 80000 | 53612 | high |
| B | 100000 | 47073 | |
| C | 35600 | 38247 | |
| D | 17800 | 17898 | middle |
| E | 6700 | 6619 | |
| F | 2222 | 2697 | |
| G | 777 | 981 | low |
| H | 8900 | 8581 | — |

Figure 14:
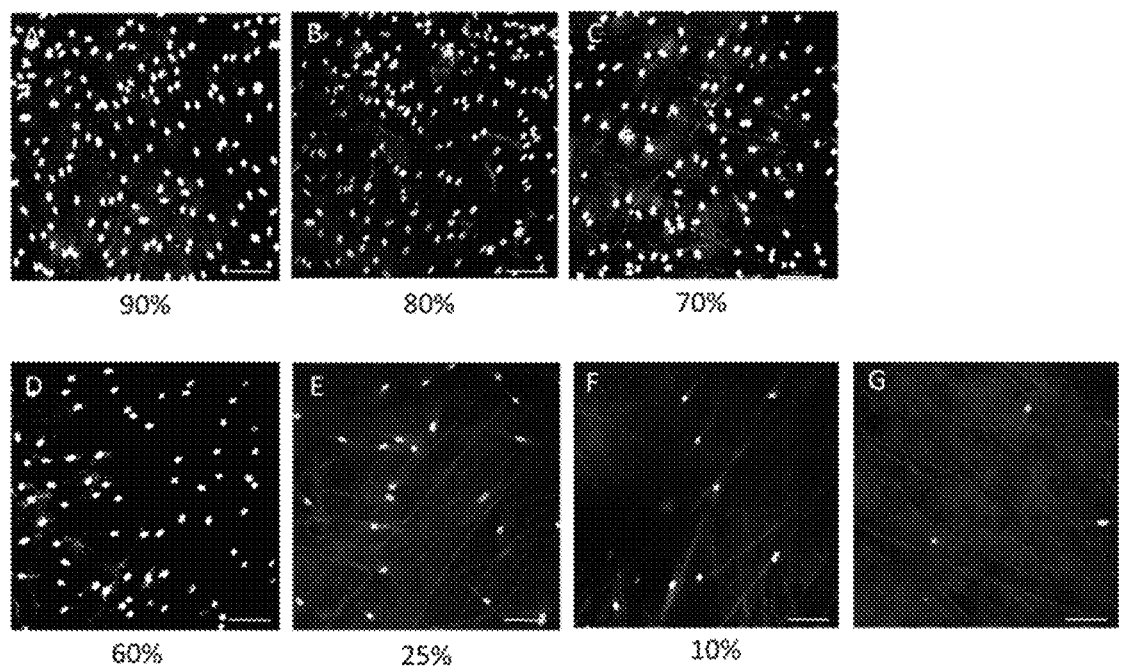
FIG. 14 includes microscope observation images of DAPI (4',6-diamidino-2-phenylindole)-stained MSCs on cell sheets with different average cell densities.

The MSCs on the cell sheets A to G were stained with DAPI (4', 6-diamidino-2-phenylindole), and were observed under a microscope (FIG. 14). The percentage confluency of MSCs on each cell sheet was measured, when the cell density of MSCs cultured on the same culture carrier until reaching confluence set to be 100% confluency. The sheets A to C reached 90% to 70% confluency, the sheets D to F reached 60% to 10% confluency, and the sheet G reached less than 10% confluency.

2. Gene Expression Analysis

Figure 15:
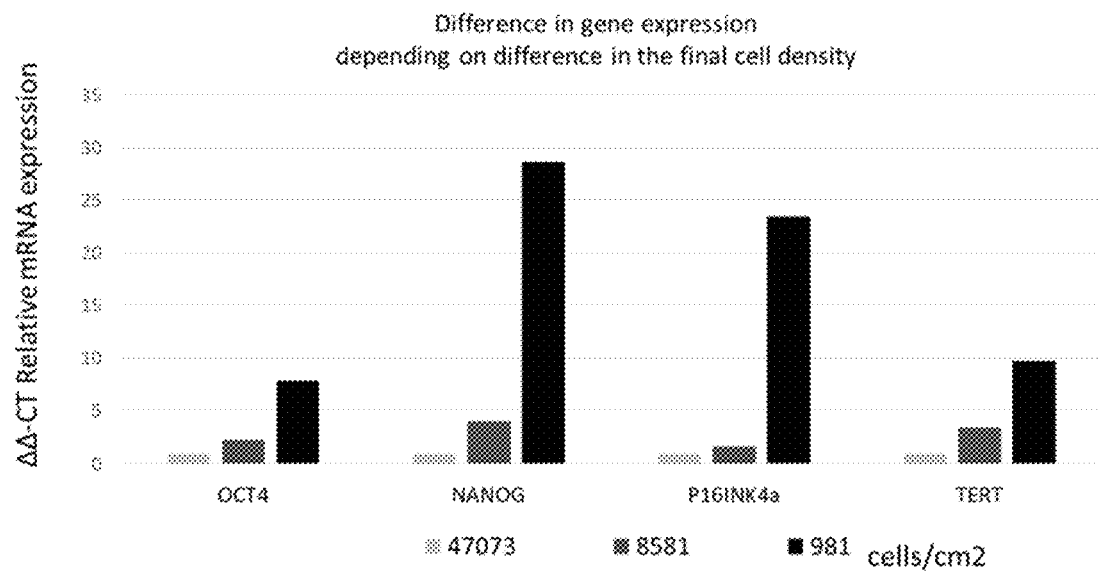
FIG. 15 is a graph illustrating the relative gene expression levels of OCT4, Nanog, p16$^{ink4a}$, and TERT in the MSCs on cell sheets B, G, and H, in comparison to those in the MSCs on the cell sheet B.

As in Example 2, the expression levels of OCT4, Nanog, $p16^{ink4a}$, and TERT in MSCs on the cell sheets B, G, and H were measured by real-time PCR (FIG. 15). The expression levels of all the genes increased as the average cell density decreased. It was estimated that the therapeutic effect of individual MSCs on cell sheet with lower average cell density was higher than that of individual MSCs on cell sheet with higher average cell density.

3. Transplantation Study in Model Rats with Acute Kidney Injury Caused by Ischemia-Reperfusion A median abdominal incision was made on 5-week-old male SD rats under anesthesia. First, the right kidney was identified, and the right renal artery was blocked with a vascular clamp. Immediately after blockage, each of the cell sheets A to G prepared in 1 described above was transplanted under the kidney fibrous capsule as in Example 3. After 60 minutes of blockade, the vascular clamp was opened and the blockage was released. For the left kidney, similarly to the above, the left renal artery was blocked, the cell sheets were transplanted, and after 60 minutes of blockade, the blockage was released (n=1 or 2/group). In addition, a group in which the Gerota's fascia, fat capsule, and fibrous capsule were removed from the kidney surface and pulled to the kidney hilus (Sham—with kidney capsule treatment), and a group in which the Gerota's fascia, fat capsule, and fibrous capsule were returned to the original position after pulled to the kidney hilus (Sham—without kidney capsule treatment), both without cell sheet transplantation, were prepared.

Figure 16:
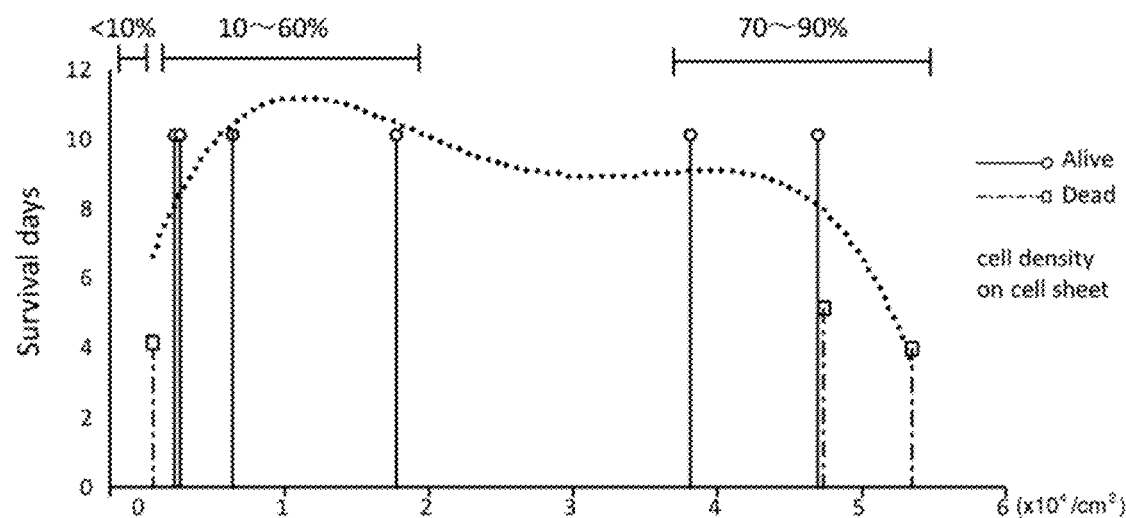
FIG. 16 is a diagram illustrating the relationship between the survival days of rats with acute kidney injury transplanted with cell sheets having different average cell densities, up to ten days after transplantation, and the average cell densities on the cell sheets.
Figure 17:
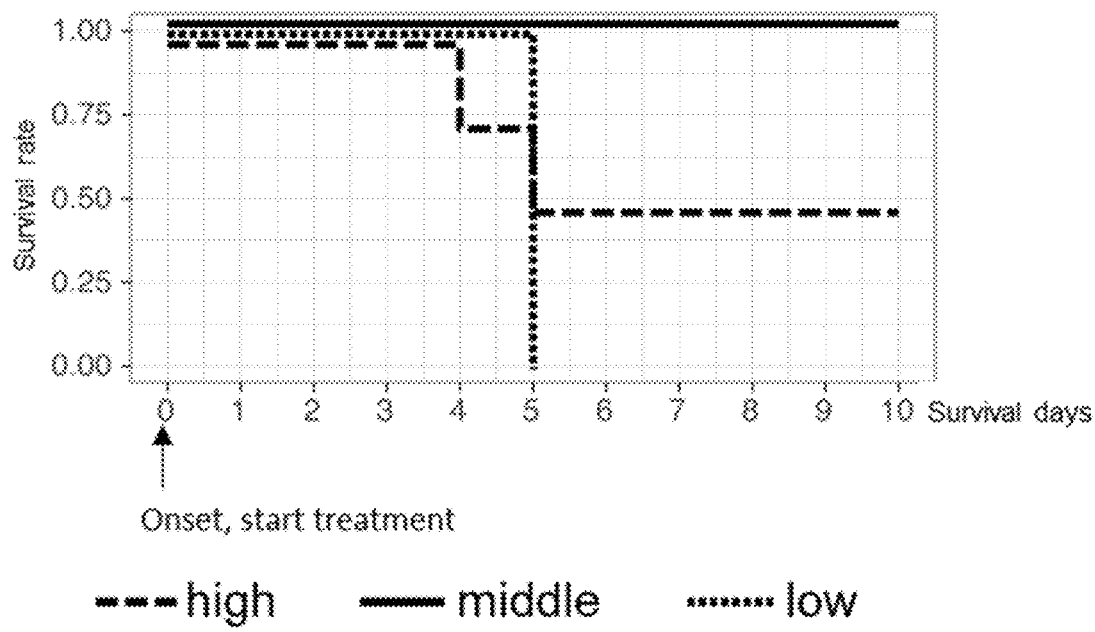
FIG. 17 is a graph illustrating the changes in the average survival rate of rats with acute kidney injury transplanted with cell sheets with different average cell densities, up to ten days after transplantation. The rats are divided into three groups according to the average cell density on the transplanted sheet.

FIG. 16 illustrates the relationship between the survival days of rats up to 10 days after transplantation, and the average cell densities on the cell sheets. FIG. 17 illustrates the Kaplan-Meier curves representing the survival rates for each group with (high, medium, and low) average cell densities. All rats transplanted with the sheets D to F with medium average cell density survived up to 10 days after transplantation, whereas half of the rats transplanted with the sheets A to C with high average cell density, and the rat transplanted with the sheet G with low average cell density died up to 10 days. The above results for the sheets A to C, where the absolute number of MSCs is high, are presumed to be due to the low therapeutic effect of individual MSCs. In addition, the above result for Sheet G, where the therapeutic effect of individual MSCs appears to be the highest, is presumed to be due to an insufficient absolute number of cells required to exert the therapeutic effect.

Figure 18:
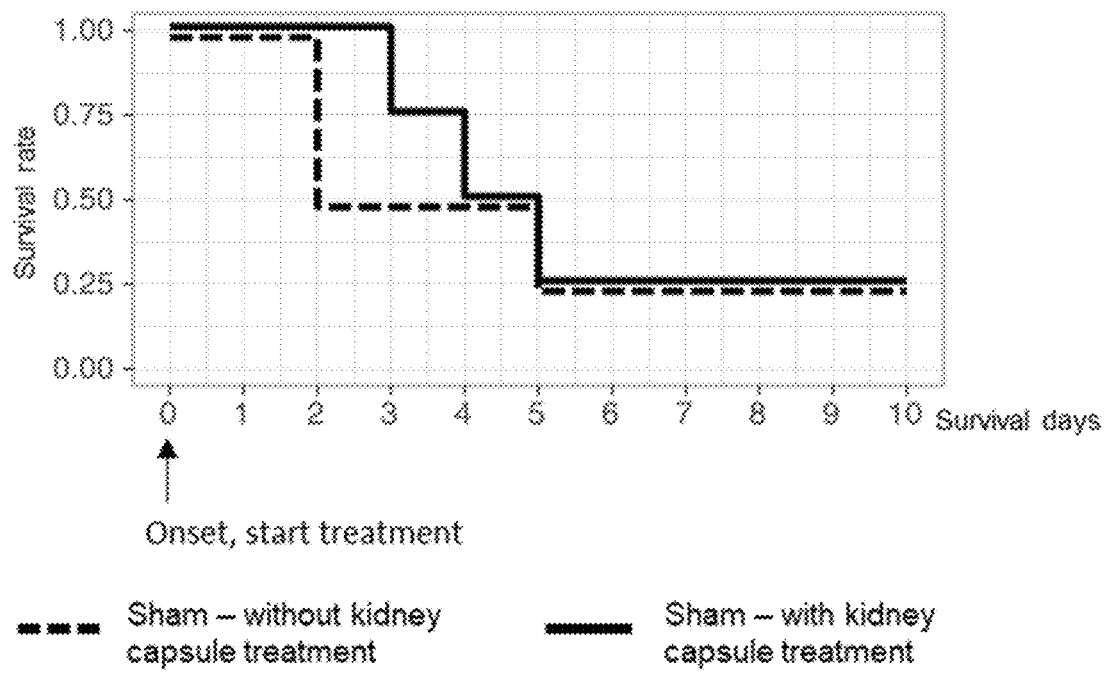
FIG. 18 is a graph illustrating the changes in the average survival rate of rats with acute kidney injury with or without kidney capsule treatment, up to ten days after transplantation.

FIG. 18 illustrates the Kaplan-Meier curves representing the survival rate of a Sham group with kidney capsule treatment and a Sham group without kidney capsule treatment, up to 10 days after transplantation. The survival rate of the Sham group with kidney capsule treatment decreased more slowly than that of the Sham group without kidney capsule treatment. Therefore, the effects of acute kidney injury were found to be alleviated by removing the Gerota's fascia, fat capsule, and fibrous capsule from the kidney surface, and separating them away from the kidney parenchyma.

Example 7 Therapeutic Effect of Cell Sheet on Alzheimer's Disease

1. Preparation of Cell Sheet

Following the method described in 1 in Example 6, cell sheets containing MSCs with different average cell densities were prepared, by seeding MSCs with the number of cells listed in Table 3 on a piece of 2.5 cm×2.5 cm substrates B, and culturing the MSCs in the MSC culture medium without an activator.

TABLE 3

| Cell Sheet | Number of Seeded Cells ($\times 10^4$ cells/cm$^2$) | Average Cell Density ($\times 10^4$ cells/cm$^2$) |
| --- | --- | --- |
| a | 8.67 | 3.19 |
| b | 0.65 | 1.45 |
| c | 0.87 | 0.41 |
| d | 0.22 | 0.37 |
| e | 0.07 | 0.18 |

2. Transplantation Study in Model Mice with Alzheimer's Disease

Fifteen-month-old male APP/PS1 mice (Charles River) were craniotically opened under isoflurane inhalation anesthesia to create a fenestration of 8 mm×5 mm from bregma level to lambda level. A piece of cell sheet cut to a size of 8 mm×5 mm was attached to the brain surface through the fenestration, and left to stand for 5 minutes. The skull was then moved back and sutured.

A novel object recognition test was performed in the third week after transplantation, the contents of which are as follows. On day 0, the mouse was placed in an empty box for 5 minutes to allow the mouse to adapt to the environment. On day 1, the mouse was placed in a box containing two identical objects for 5 minutes (familiarization). An hour later, one of the objects was replaced by a novel object, and the time the mouse spent exploring the novel object or the existing object in 5 minutes was measured. The ratio of time the mice spent exploring the novel object with respect to the total time the mice spent exploring the two objects (preference index; time spent exploring novel/(time spent exploring novel+time spent exploring existing object)×100%) was calculated, and 50% or more was defined to have good cognitive function. The objects were placed on the same positions throughout the test.

Figure 19:
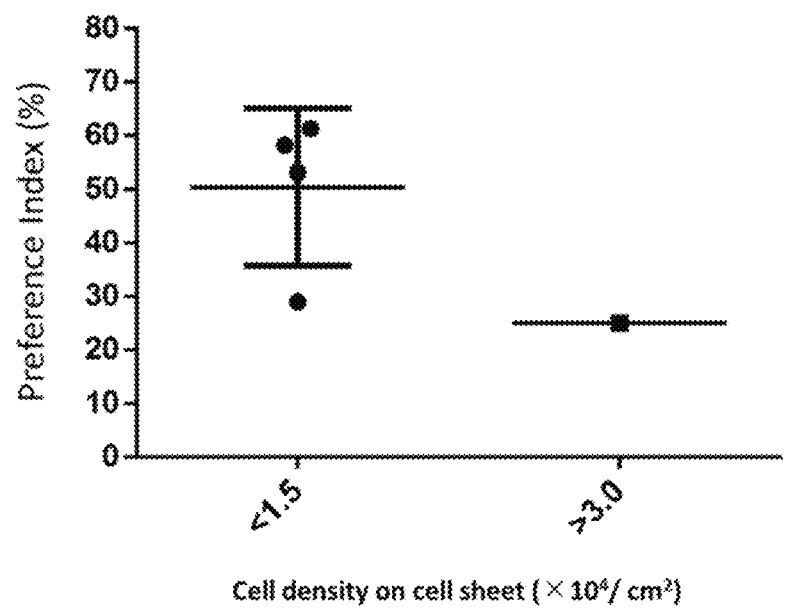
FIG. 19 is a graph illustrating the results of a novel object recognition test on Alzheimer's disease model mice transplanted with cell sheets with different average cell densities. The mice are divided into two groups according to the average cell density on the transplanted sheet.

FIG. 19 illustrates the results of plotting the preference index in two groups into which the mice were divided according to the average cell density of the transplanted sheets. The mice transplanted with the sheet of $1.50 \times 10^4$ cells/cm$^2$ or less had a high preference index, and a good cognitive function. Therefore, the cell sheet according to the present invention was further found to have a therapeutic effect on Alzheimer's disease.

Example 8 Effect of Cell Sheet Using Mouse Adipose Tissue-Derived MSCs on Kidney Disease 1. Preparation of Cell Sheet Epididymal fat of C57BL/6 (male, 10 week old) was collected, and cut into small pieces. Then, PBS containing 0.4 PZ units/mL Liberase (trademark) was added at 1 mL per gram of fat, and left to stand at 37° C. for 2 hours. 5 mL of DMEM containing 10% FBS was then added and suspended. The supernatant was removed by centrifugation at 300 g for 5 minutes. The cell pellets collected from 1 g fat were seeded on a one 15-cm dish, and cultured in DMEM containing 10% FBS and 1% PS for 4 days. After changing the culture medium, adherent cells (mouse adipose tissue-derived MSCs) were collected.

Figure 20:
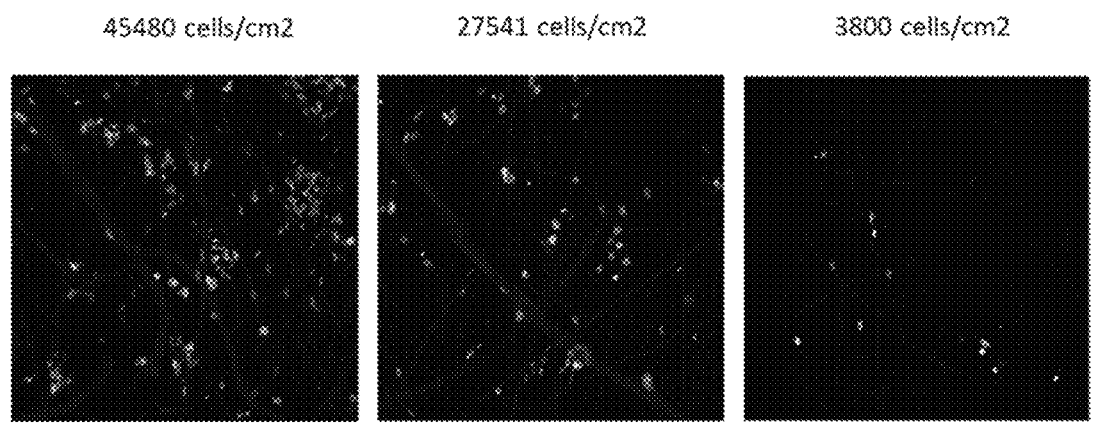
FIG. 20 includes DAPI-stained microscope observation images of adipose-tissue-derived MSCs on cell sheets with different average cell densities.

The mouse adipose tissue-derived MSCs of $6 \times 10^4$/cm$^2$, $3 \times 10^4$/cm$^2$, and $4 \times 10^3$/cm$^2$ were seeded on a piece of 1×0.8 cm NEOVEIL nano (Gunze Co., Ltd.), respectively, and 2 mL of the MSC culture medium without an activator was added. The MSCs were then cultured at 37° C. for 24 hours to produce cell sheets at passage 1 on which the final cell densities (mean±standard error, DAPI stained cell number) after culture were 45,480±4,953/cm$^2$, 27,541±5,475/cm$^2$, and 3,800±908/cm². FIG. 20 shows microscope observation images of DAPI-stained MSCs on each of the cell sheets.

2. Transplantation Study in Model Mice with Acute Kidney Injury Caused by Ischemia-Reperfusion An incision was made in the right back of 10 to 11-week-old male C57BL6 mice under anesthesia to expose the right kidney. The right renal artery and vein were ligated and transected, and the right kidney was removed. After confirming no hemorrhage, the kidney was returned to its original position in the body, and the skin was closed. Next, an incision was made in the left back, the left kidney was exposed, and the blood flow of the left renal artery and vein was blocked with a noninvasive vascular clip. During the 22 minutes of blockage, the Gerota's fascia, fat capsule, and fibrous capsule were carefully incised and removed from the kidney surface so as not to damage the adrenal gland, and pulled to the kidney hilus. Cell sheets of 45,480 cells/cm² (n=4), 27,541 cells/cm² (n=4), or 3,800 cells/cm² (n=3) were attached to the kidney so as to cover the whole kidney. Twenty-two minutes after the start of ischemia of the left kidney, the clip was removed and the blood was reperfused. As controls, a group of mice in which the right kidney was removed, ischemia was performed on the left kidney for 22 minutes, and was reperfused without cell sheet transplantation (Sham group: n=3); and untreated normal mice (n=4) were prepared.

Figure 21:
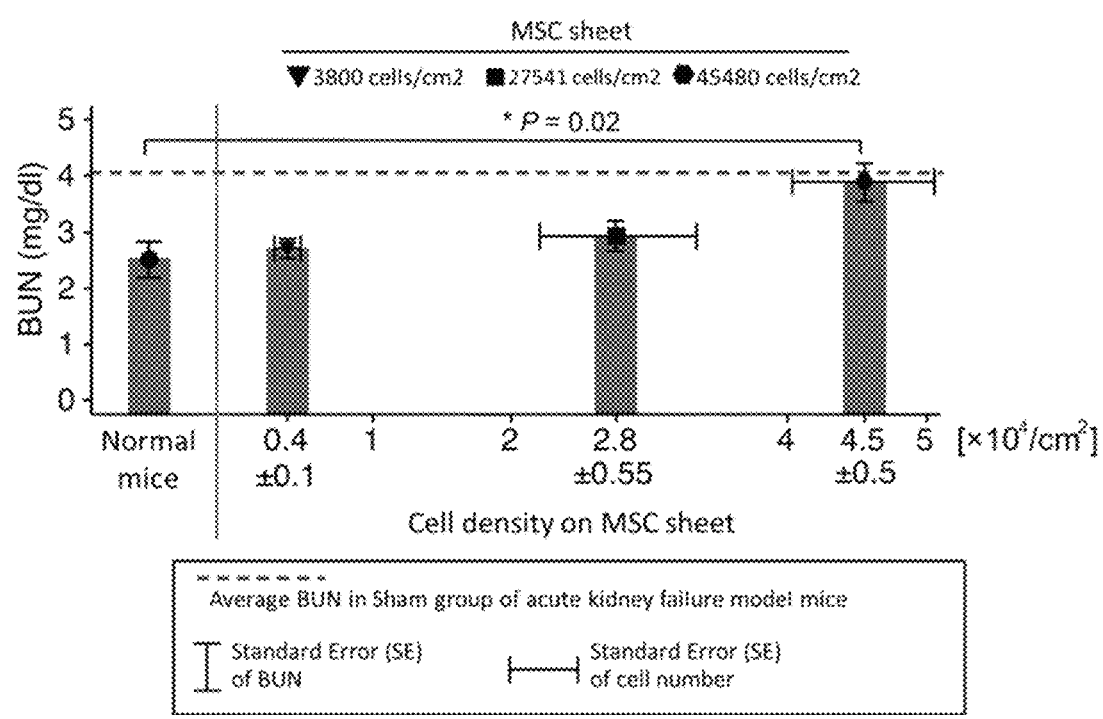
FIG. 21 is a graph illustrating blood urea nitrogen in mice with acute kidney injury transplanted with a cell sheet containing mouse adipose-tissue-derived MSCs, 24 hours after transplantation.

Blood were collected from the mice 24 hours after attaching the cell sheet. Urea nitrogen (BUN) was measured using a UV method (SRL). The results are shown in FIG. 21. The BUN in the group transplanted with the cell sheet having high cell density (45,480 cells/cm²) was comparable to that in the Sham group, indicating the progression of acute kidney injury, whereas the BUN in the group transplanted with the cell sheet having medium cell density or low cell density (27,541 cells/cm² or 3,800 cells/cm²) was comparable to that in normal mice. Based on these results, it was confirmed that the cell sheet according to the present invention using MSCs derived from mouse adipose tissue, as well as the cell sheet according to the present invention using MSCs derived from human bone marrow, was effective in suppressing the progression of acute kidney injury.

The invention claimed is:

1. A cell sheet for transplantation into a living body,
containing mesenchymal stem cells and a biocompatible support,
wherein the average cell density of the mesenchymal stem cells on the cell sheet is from $3.0 \times 10^3$ cells/cm$^2$ to $3.0 \times 10^4$ cells/cm$^2$,
the support is a cell culture carrier whose cell contact surface consists of a three-dimensional structure formed of a fiber that has an average fiber diameter of from nanometer order to micrometer order and that is stacked in a three-dimensional direction, and
the cell sheet is prepared by a method comprising a step of culturing mesenchymal stem cells on the cell culture carrier so that the average cell density becomes from $3.0 \times 10^3$ cells/cm$^2$ to $3.0 \times 10^4$ cells/cm$^2$.

2. The cell sheet according to claim 1, wherein the cell culture carrier has openings formed of a fiber having an average fiber diameter of from nanometer order to micrometer order on the cell contact surface.

3. The cell sheet according to claim 2, wherein the openings have an average diameter ranging from 500 nm to 1,000 μm.

4. The cell sheet according to claim 1, wherein the support is a cell culture carrier containing a nanofiber made of a biodegradable polymer.

5. The cell sheet according to claim 1, wherein the mesenchymal stem cells are mesenchymal stem cells derived from bone marrow or adipose tissue.

6. The cell sheet according to claim 1, wherein the mesenchymal stem cells are mesenchymal stem cells separated from a subject suffering from a disease.

7. A method comprising locally applying to a subject with the cell sheet of claim 1.

8. The method according to claim 7, wherein the subject has a disease selected from the group consisting of diabetes and the complication thereof; cerebrovascular disease; cerebral degeneration disease; demyelinating disease; functional and seizure disorders; dementing disorder; peripheral nerve disease; cardiovascular disease; autoimmune disease; liver, biliary tract, and pancreas diseases; gastric and duodenal diseases; small and large intestine and colon diseases; thyroid disease; hematologic and hematopoietic diseases; lung disease; kidney disease; eye disease; skin disease; muscular and bone diseases; trauma; and graft-versus-host disease (GVHD).

9. The method according to claim 8, wherein the disease is a kidney disease, and wherein the cell sheet is applied under a kidney fibrous capsule.

10. The method according to claim 8, wherein the disease is brain injury or neurodegenerative disease, and wherein the average cell density of the mesenchymal stem cells on the cell sheet is from $3.0 \times 10^3$ cells/cm$^2$ to $1.5 \times 10^4$ cells/cm$^2$.

11. The method according to claim 10, wherein the cell sheet is applied to a site of brain injury, a site of brain degeneration, or a vicinity thereof.

12. The method according to claim 7, wherein the mesenchymal stem cells are mesenchymal stem cells derived from bone marrow or adipose tissue.

13. The method according to claim 7, wherein the mesenchymal stem cells are mesenchymal stem cells separated from a subject suffering from a disease.

* * * * *